United States Patent
Kumpan-Bahrami et al.

(10) Patent No.: US 11,950,682 B2
(45) Date of Patent: Apr. 9, 2024

(54) METHOD AND DEVICE FOR PROVIDING A HAIR TREATMENT AGENT

(71) Applicant: Henkel AG & Co. KGaA, Duesseldorf (DE)

(72) Inventors: Esther Kumpan-Bahrami, Duesseldorf (DE); Jordan Katzarov, Duesseldorf (DE); Georg Knuebel, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 668 days.

(21) Appl. No.: 16/617,888

(22) PCT Filed: May 29, 2018

(86) PCT No.: PCT/EP2018/063988
§ 371 (c)(1),
(2) Date: Nov. 27, 2019

(87) PCT Pub. No.: WO2018/219895
PCT Pub. Date: Dec. 6, 2018

(65) Prior Publication Data
US 2020/0113313 A1    Apr. 16, 2020

(30) Foreign Application Priority Data
May 31, 2017 (DE) ................ 10 2017 209 227.0

(51) Int. Cl.
*A45D 44/00* (2006.01)
*A45D 19/00* (2006.01)
(Continued)

(52) U.S. Cl.
CPC .......... *A45D 44/00* (2013.01); *A45D 19/012* (2021.01); *A61B 5/0077* (2013.01);
(Continued)

(58) Field of Classification Search
CPC ............... A45D 44/00; A45D 19/012; A45D 2044/007; A61B 5/0077; A61B 5/1032;
(Continued)

(56) References Cited

U.S. PATENT DOCUMENTS 6,817,222 B2 * 11/2004 Day .................. G01N 33/4833
73/9
2004/0105830 A1 * 6/2004 Boswell .................. A61Q 5/04
424/70.2
(Continued)

FOREIGN PATENT DOCUMENTS

WO    0123850 A1    4/2001
WO    0224071 A2    3/2002
(Continued)

OTHER PUBLICATIONS

EPO, International Search Report and Written Opinion issued in International Application No. PCT/EP2018/063988, dated Jul. 19, 2018.

*Primary Examiner* — Eric F Winakur
*Assistant Examiner* — Abid A Mustansir
(74) *Attorney, Agent, or Firm* — Lorenz & Kopf, LLP

(57) ABSTRACT

In various embodiments, a method of providing a hair treatment agent is provided. The method can have a detecting of at least one sensor value on hair of a user by employing at least one portable sensor, a determining of a hair condition of the user by employing the detected at least one sensor value, a computer-assisted determining of a user-specific hair treatment agent including the determined hair condition, and a preparing of the determined user-specific hair treatment agent by employing a hair treatment agent mixing device.

13 Claims, 13 Drawing Sheets

(51) Int. Cl.
*A61B 5/00* (2006.01)
*A61B 5/103* (2006.01)

(52) U.S. Cl.
CPC ............ *A61B 5/1032* (2013.01); *A61B 5/448* (2013.01); *A61B 5/6898* (2013.01); *A45D 2044/007* (2013.01); *A61B 2562/0204* (2013.01)

(58) Field of Classification Search
CPC .................. A61B 5/448; A61B 5/6898; A61B 2562/0204; A61B 5/0013; A61B 5/339; A61B 5/4839
See application file for complete search history.

(56) References Cited

U.S. PATENT DOCUMENTS

| | | |
|---|---|---|
| 2010/0139682 A1 | 6/2010 | Edgar et al. |
| 2014/0118521 A1* | 5/2014 | Conti .................... G01J 3/0264 |
| | | 348/E7.085 |
| 2015/0342515 A1 | 12/2015 | Hutchings et al. |

FOREIGN PATENT DOCUMENTS

| | | |
|---|---|---|
| WO | 2012127429 A2 | 9/2012 |
| WO | 2017032636 A1 | 3/2017 |

\* cited by examiner

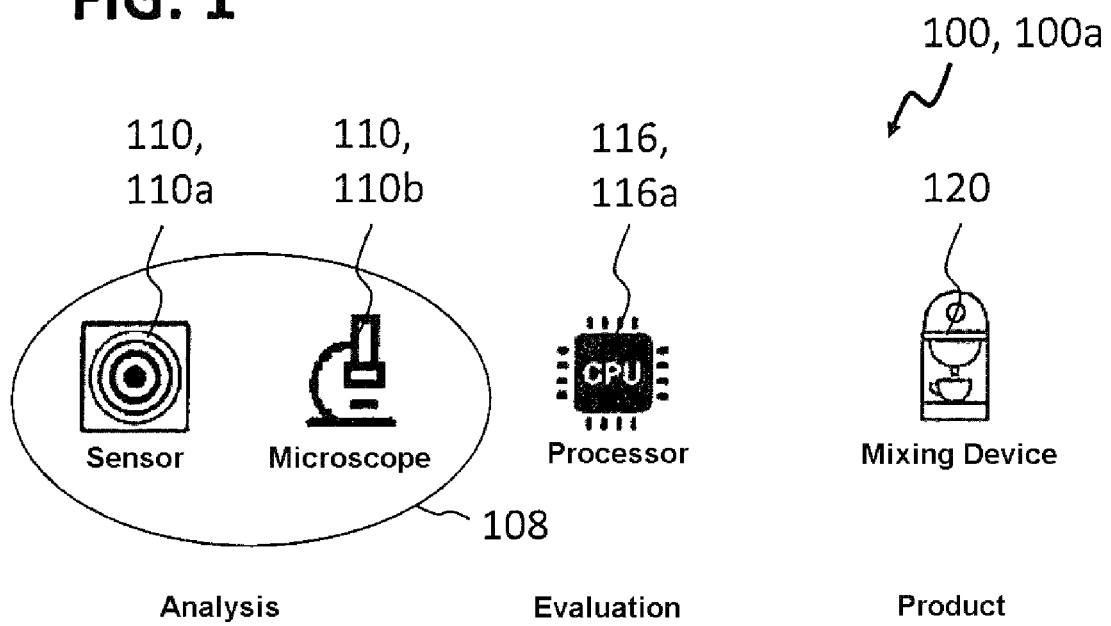
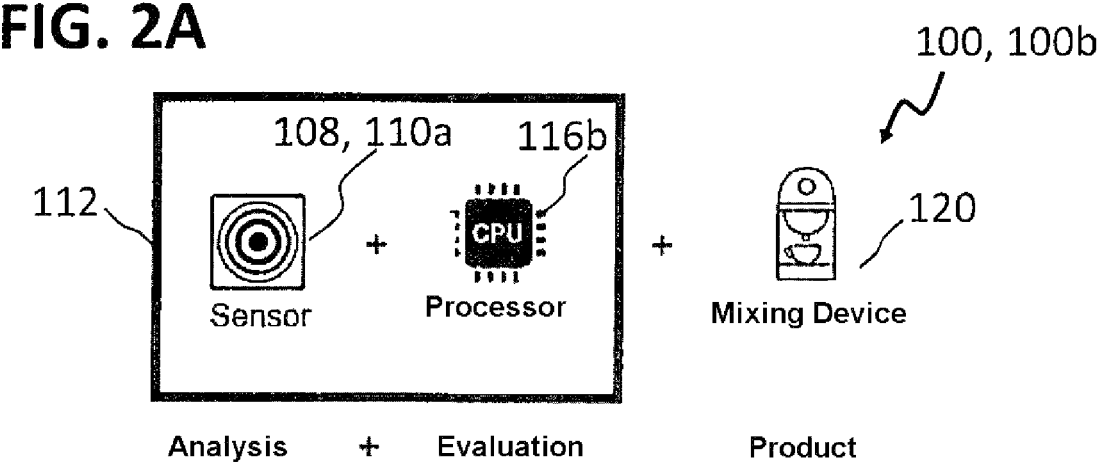

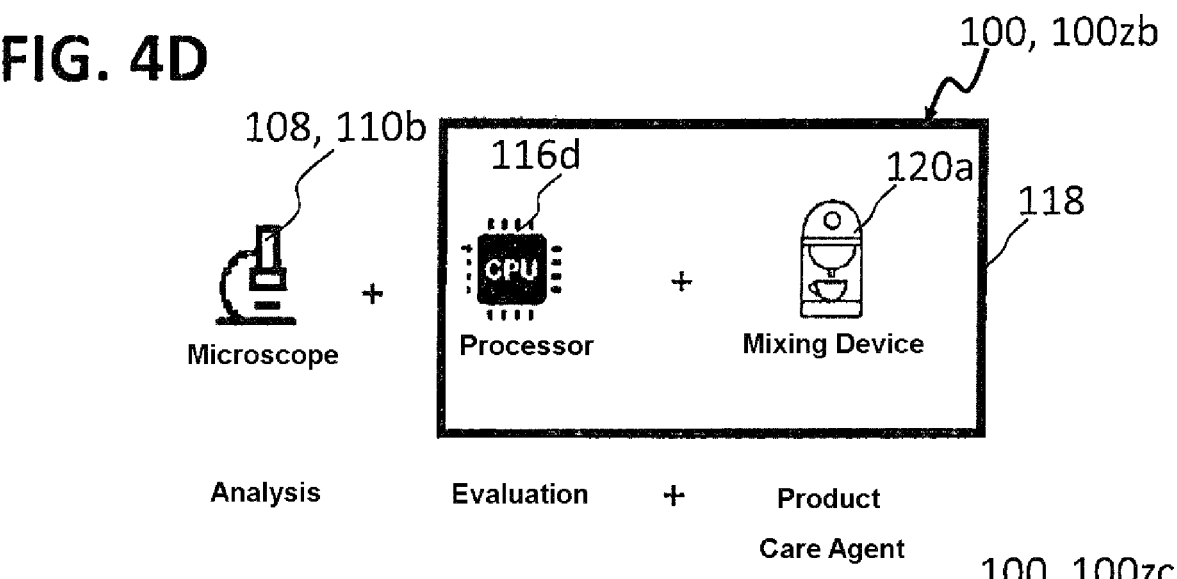
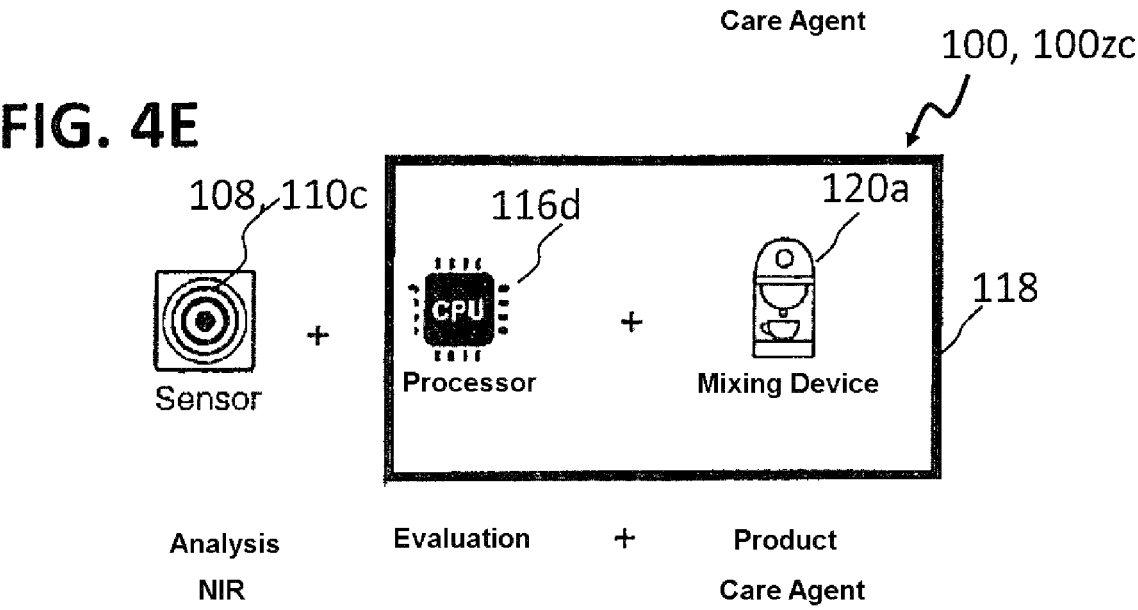
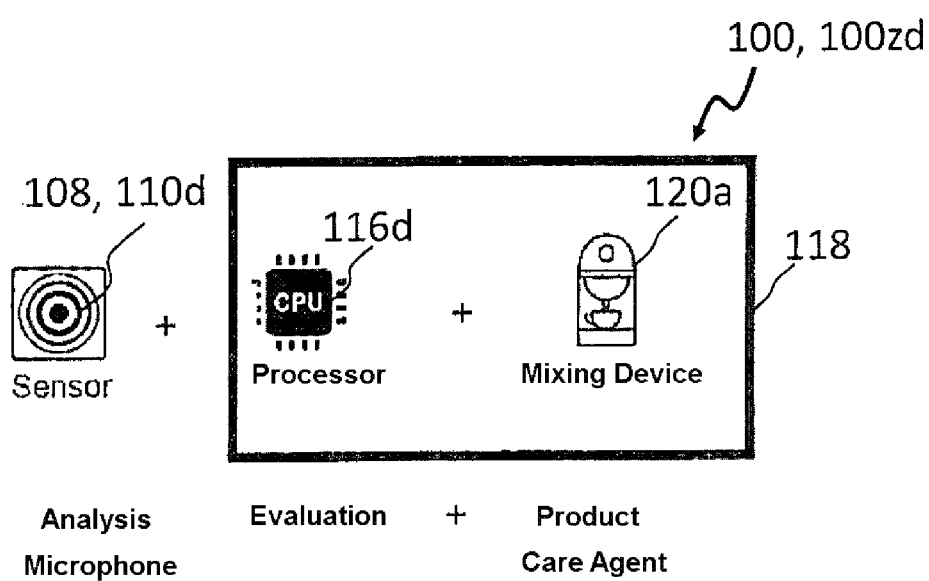

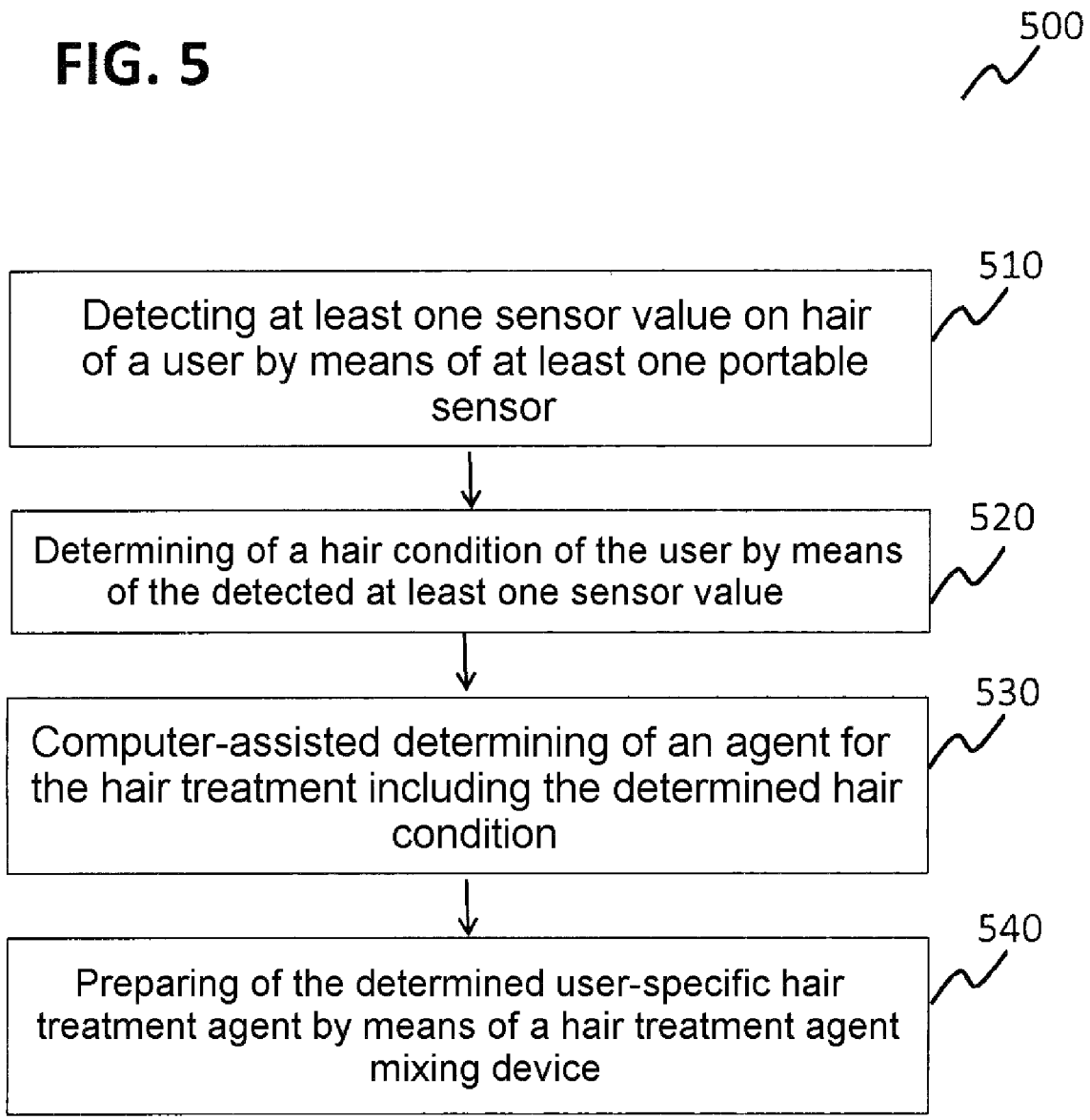

METHOD AND DEVICE FOR PROVIDING A HAIR TREATMENT AGENT

CROSS-REFERENCE TO RELATED APPLICATION

This application is a U.S. National-Stage entry under 35 U.S.C. § 371 based on International Application No. PCT/EP2018/063988, filed May 29, 2018, which was published under PCT Article 21(2) and which claims priority to German Application No. 10 2017 209 227.0, filed May 31, 2017, which are all hereby incorporated in their entirety by reference.

TECHNICAL FIELD

The present disclosure relates to a method and device for providing a hair treatment agent.

BACKGROUND

In many areas of daily life, there has been a trend towards personalized programs that can respond to individual requirements and needs, for example, in a nutrition or health area, but also in an area of personalized cosmetics. This can enable a user to find targeted cosmetic products and/or to obtain care instructions that are matched to the individual needs of his hair, and thus enable a particularly high effectiveness.

When treating hair with cosmetic products, an effect of the product, for example, intensity of coloring, effectiveness of a care product, or hair deformation action of a permanent wave, can greatly depend on a degree of damage of the hair.

Determining damage to the hair can therefore be very important.

Some, in particular young, hairdressers can lack the experience of how to deal with damaged hair, for example, which care products are suitable and/or how a hair coloring agent (also referred to as hair coloring) is to be mixed in order to achieve the desired color result despite the damaged hair.

The hair can be damaged through natural or artificially induced processes. The most important type of damage in this case can be oxidative damage.

The natural processes may, for example, have a combined (for example, simultaneous) action of UV light and oxygen ($O_2$) on the hair.

The artificially induced processes in this case can have, for example, applying hair coloring agents (also referred to as colorings, which also includes bleaching), and/or a styling or shaping of the hair (for example, creating a permanent wave).

In addition to desirable cosmetic effects, such as a lightening of the hair, it is also possible for severe damage to the hair to occur, for example, when using oxidizing agents.

In the case of damaged hair, for example, a cysteic acid content may be increased due to an oxidation of the amino acids cystine and cysteine, which occur very frequently in the hair, to cysteic acid.

Besides cystine and cysteine, other amino acids present in human hair can also be oxidized.

Oxidation of cystine/cysteine to cysteic acid can destroy the mechanical stability of the hair and even lead to complete hair breakage with multiple applications. However, previously macroscopically perceptible, for example, tangible, properties of the hair, for example, a surface condition, for example, a surface roughness, can be negatively influenced. For example, damaged hair can have higher surface roughness than undamaged hair.

BRIEF SUMMARY

Human hair includes proteins, lipids, water, trace elements and pigments. The fiber protein keratin is the main constituent of the hair. The lipids present in human hair are either free or covalently bound. Melanins are reddish, brown or black pigments, which cause the coloring of the hair.

Results of cosmetic treatments can depend on further properties of the hair being treated, for example, (in particular in the case of coloring) of a hair color, a hair structure (in particular in a styling, for example, a permanent wave, a smoothing, etc.), a moisture content (for a care product), etc.

Therefore, a determining of the composition of the hair in terms of the amino acids, lipids and melanins present and the water content can be of great importance.

Conventional commercially available hair treatment products are available as a limited range of products for a given application. For example, every hair color manufacturer provides a limited range of hair coloring agents. Even if a degree of hair damage of the user can be known before dyeing (possibly in addition to his initial hair color), for example, from laboratory measurements, it may therefore be impossible to achieve a desired result, but rather usually, at most, a result close to the desired result can be achieved.

In addition, it may not be practical to compile the degree of hair damage and possibly further hair condition parameters such as the hair condition (for example, hair color, hair texture, etc.) based on measurements made by, for example, various laboratories and/or various devices to determine a hair treatment product.

BRIEF SUMMARY

Devices and methods for providing a hair treatment agent are provided herein. In an embodiment, a device for providing a hair treatment agent includes a portable sensor device, a data processing device, and a hair treatment agent mixing device. The portable sensor device has at least one sensor for the detecting at least one sensor value on hair of a user. The data processing device is configured to determine a hair condition of the user by employing the detected at least one sensor value. The data processing device is also configured for the computer-assisted determining of a user-specific hair treatment agent using the determined hair condition. The hair treatment agent mixing device is configured for preparing the determined user-specific hair treatment agent.

In another embodiment, a method of providing a hair treatment agent employs the device as described above. The method includes detecting at least one sensor value on hair of a user by employing a sensor device having at least one portable sensor. A hair condition of the user is determined by employing the detected at least one sensor value, wherein determining the hair condition includes determining a degree of damage of the hair and/or hair status. A user-specific hair treatment agent is determined with computer assistance using the determined hair condition. The determined user-specific hair treatment agent is prepared by employing a hair treatment agent mixing device.

In another embodiment, a device for providing a hair treatment agent includes a portable sensor device, a data processing device, and a hair treatment agent mixing device. The portable sensor device has at least one optical sensor for determining a hair ingredient and a microphone for determining a surface roughness of the hair. The data processing device is configured to determine a degree of damage of hair of a user by employing detected sensor values from the optical sensor and the microphone. The data processing device is also configured for the computer-assisted determining of a user-specific hair treatment agent using the determined hair condition. The hair treatment agent mixing device is configured for preparing the determined user-specific hair treatment agent. The hair treatment agent mixing device includes a mixing device for producing a hair care agent, a hair coloring agent and/or a hair styling agent.

BRIEF DESCRIPTION OF THE DRAWINGS

The present disclosure will hereinafter be described in conjunction with the following drawing figures, wherein like numerals denote like elements, and:

FIGS. 1, 2A to 2K, 3A to 3M and 4A to 4K each show a schematic illustration of a device for providing a hair treatment agent according to various embodiments; and FIG. 5 illustrates a flow chart of a method of providing hair treatment agent according to various embodiments.

DETAILED DESCRIPTION

Figure 2B:
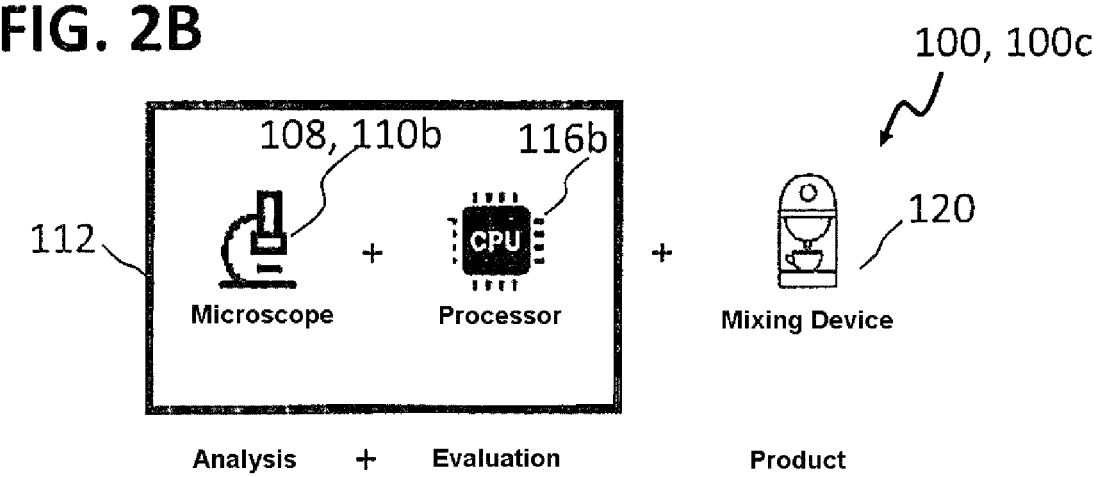

The following detailed description is merely exemplary in nature and is not intended to limit the disclosure or the application and uses of the subject matter as described herein. Furthermore, there is no intention to be bound by any theory presented in the preceding background or the following detailed description.

In various embodiments, a system is provided for providing a hair treatment product which makes it possible to determine a hair condition of a user and to determine a hair treatment product individually matched to the hair condition based on the determined hair condition and to manufacture it in a mixing device for the user.

The hair condition can have a hair damage and/or a hair status.

The hair damage can be an oxidative hair damage or a mechanical hair damage in various embodiments.

The hair status can in particular have a hair color, a content of a hair ingredient, a hair thickness, a curliness of hair and/or a gray portion of hair.

In particular, the hair ingredient can comprise water, melanins, lipids, amino acids, and mixtures thereof. A preferred hair ingredient, the content of which is determined to determine hair status, is water.

In addition to the 20 canonical amino acids glycine, alanine, valine, isoleucine, leucine, phenylalanine, tyrosine, lysine, arginine, histidine, aspartic acid, glutamic acid, threonine, serine, glutamine, asparagine, methionine, cysteine, proline and tryptophan, human hair further contains the amino acids cystine, omithine and citrulline. Accordingly, it is preferable that the hair ingredient, the content of which is determined, is an amino acid selected from the group of glycine, alanine, valine, isoleucine, leucine, phenylalanine, tyrosine, lysine, arginine, histidine, aspartic acid, glutamic acid, threonine, serine, glutamine, asparagine, methionine, cysteine, proline, tryptophan, cystine, omithine, citrulline and mixtures thereof.

The system can have a sensor device in various embodiments for the determining of the hair condition of the user. The sensor device can have at least one sensor, for example, a plurality of sensors.

Reference can be made herein to "the sensors", for example, with respect to data transmission between the sensors and the data processing device, an arrangement of sensors, etc. It is to be understood that the sensors can have a totality of sensors and/or sensor circuits arranged in the sensor device, for example, a totality of microphone(s), optical sensor(s) (for example, spectrometer, camera, microscope), speed sensor circuit, etc., or, if apparent from the context, a part of said sensors and/or sensor circuits.

In various embodiments, the system can have a data processing device for the determining of the hair condition and for the determining of the hair treatment product.

In various embodiments, a "holistic ecosystem" of intelligent/smart devices can be provided which unites all functions of problem identification, that is, an analysis of the hair (by employing the sensor device), through providing advice, that is, an evaluation of the detected sensor values, to a provision of a desired benefit, for example, a hair treatment product.

In various embodiments, a hair treatment agent mixing device for preparing the determined user-specific hair treatment agent can be coupled to a (portable) sensor device and a data processing device such that a detecting of a hair condition of the user and a determining of a composition of the hair treatment agent matched to the hair condition of the user and be prepared by the mixing device can be made directly on site.

In various embodiments, the system can have three elements, namely an analysis device for hair status, for example, a comb, brush, or otherwise shaped body of the sensor device, which can have a microscope and/or another sensor, a display device, for example, a display and input device (for example, a smartphone, tablet, laptop or a so-called "smart mirror") on which an app or other suitable software can be installed, and a mixing machine for an individualized hair treatment agent, for example, a hair care product and/or a hair coloring agent. The display and input device can have a (for example, touch-sensitive) screen. Furthermore, the display and input device can be configured to determine a composition of the individualized hair treatment agent. The smart mirror can be a device that combines a function of a mirror with a function of a (for example, touch-sensitive) screen, that is, in addition to a mirroring and/or emitting light (for example, mirroring or displaying the user), can provide and/or receive and possibly evaluate information. In various embodiments, the smart mirror can be designed to provide, instead of a mirrored image of the user, a representation that acts as a mirrored image of the user, or a representation of the user in which his hair is altered, for example, according to a determined treatment result, for example, with a hair color determined as a result of hair coloring. In this case, the representation can be formed such that it acts like a mirrored image of the user with the new hair color. The representation can be dynamic, for example. The smart mirror can be formed in a substantially known manner except for differences described herein.

In various embodiments, the display and input device, such as the smart mirror, can be configured to control the mixing machine. For example, the display and input device can provide a suggestion for a composition of a hair treatment agent (for example, a hair care and/or hair coloring agent) which the user (or, for example, the hairdresser, salesman, or the like) can accept or modify. The ultimately adopted composition can be transmitted in various embodiments to the mixing machine for producing the hair treatment agent.

In various embodiments, the input device can be used to input a desired result, for example, a desired hair color, a desired care condition, a desired styling (for example, curls with a stepped curl, or the like).

In various embodiments, the device for providing the hair treatment agent, when determining the hair treatment agent, can take into account the desired result, such that the hair treatment agent determined and subsequently provided by the hair treatment agent mixing device is suitable for producing the desired result on the hair of the user.

In various embodiments, the display and input device can form an integrated unit with the sensor device, for example, when using a camera and/or a microphone of a smartphone as a sensor, or for example, in which a near-infrared spectrometer is equipped with a data processing device and a, for example, touch-sensitive display. In various embodiments, the sensor device is a component of a smart terminal, preferably a smartphone or a tablet.

In various embodiments, the hair treatment agent mixing device can form an integrated unit with the display and input device, for example, in which the hair treatment agent mixing device is equipped with the data processing device and the display and input device in the form of a, for example, touch-sensitive screen. The display and input device can be configured to be used for initiating a measurement by employing the sensor device coupled to the hair treatment agent mixing device.

In various embodiments, at least one of the sensor device, the data processing device, and the hair treatment agent mixing device can have, in addition to the display device or alternatively, an acoustic output device, for example, a speaker.

In various embodiments, at least one of the sensor device, the data processing device, and the hair treatment agent mixing device can have, in addition to the touch-sensitive screen, as an input device or, alternatively thereto, an acoustic input device, for example, a microphone.

In a case where the sensor device has the microphone, the microphone can also be used in various embodiments as an input microphone.

In various embodiments, alternatively or additionally, another conventional input device can be provided as input device, for example, a keyboard, a mouse, etc.

In various embodiments, a plurality of individual components can be provided in the mixing device, which components can be mixed based on the determined composition to produce the user-specific hair treatment agent. The plurality of individual components can have, for example, a plurality of hair coloring components for producing a hair coloring agenting agent, a plurality of hair care components for producing a hair care agent or a plurality of hair styling components for producing a hair styling agent.

In various embodiments, the plurality of components can have at least one base component and a plurality of supplemental components, wherein the supplemental components can be mixed with the base component in a composition (for example, a proportion) determined by the method.

In order to provide the care agent, in various embodiments, a plurality of (supplementary) components having different care performances can be provided in the hair treatment agent mixing device. The components can have known care substances such as quaternary nitrogen compounds (for example, hexadecyltrimethylammonium chloride), cationic polymers (for example, those of INCI (International Nomenclature of Cosmetic Ingredients) Polyquaternium-10), silicones and/or dicarboxylic acid (for example, succinic acid or maleic acid). In said components, a care performance can increase from the quaternary nitrogen compounds via the cationic polymers and the silicones to the dicarboxylic acid. In various embodiments, other or further known care substances can be used instead or in addition thereto. Suitable care products comprise, in particular, conditioners, hair treatments, hair masks or 2-in-1 shampoos.

To provide the cosmetic hair care composition, in various embodiments, one or more of the components can be added as a supplemental component(s) to the base component to form the determined hair care product. A weight fraction of a respective supplemental component can typically be in a range of less than about 1% to a few percent.

In order to provide the care agent, in various embodiments, a plurality of (supplementary) components having different shades can be provided in the hair treatment agent mixing device. The "different shades" are to be understood to mean that, when dyeing, the different components on the same standard hair sample would lead to different color results.

In various embodiments, the hair coloring agent components provided in the hair treatment agent mixing device can be known dye precursors which form color pigments only in the hair, such as, for example, p-tolylene-diaminesulfate, m-aminophenol, toluene-2,5-diamines, 4-toluenediamine, p-aminophenol, phenylenediamine, 4-phenylenediamine and/or others.

Alternatively or additionally, the hair coloring agent components provided in the hair treatment agent mixing device in various embodiments can have direct coloring components (direct dyes), that is, those which are not dye precursors but rather already have color pigments before contact with the hair.

In various embodiments, when determining the composition of the hair treatment agent, the data processing device can be configured to consider which components the hair treatment agent mixing device holds ready.

In various embodiments, the dye components held ready in the hair treatment agent mixing device can be chosen so that the widest possible spectrum of possible hair colors can be achieved by combining the components with each other. In other words, the dye components held ready can be chosen so that a color space accessible by employing dyeing has the largest possible area or (depending on the parameterization) a largest possible volume.

In various embodiments, the dye components held ready in the hair treatment agent mixing device can be selected so that for particularly popular hair color ranges, that is, those color ranges for which there is a higher probability of them being requested (for example, a hair color range around a henna shade or a hair color range around a aubergine shade), such a fine gradation of the hair colors achievable by employing the hair coloring agent provided by the hair treatment agent mixing device, that, at least for the at least one popular hair color range, complete coverage is achieved so that the hair coloring agent can be provided so that a color difference between the expected hair color result and a desire hair color always lies below a threshold of human perception.

To provide the hair coloring agent, one or more of the components in various embodiments can be added to the base component as supplemental component(s) to form the determined hair coloring agent.

In order to provide the hair styling agent, in various embodiments, a plurality of (supplementary) components having different styling effects can be provided in the hair treatment agent mixing device. The components can have known hairstyling agent components, for example, for producing a permanent wave, by employing which the hair can be permanently waved or smoothed, for example. A permanent wave is typically produced in two stages by applying two different agents (a waving agent and a fixing agent) to the hair. Accordingly, the hair treatment agent mixing device can be configured to produce both agents. To produce the waving agent, the hair treatment agent mixing device can have, for example, one or more known reducing agents, pH buffers, emulsifiers, etc. as supplementary components. To produce the fixing agent, the hair treatment agent mixing device can, for example, respectively have one or more known oxidizing agents, emulsifiers, etc. as supplementary components.

In various embodiments, the styling agent can have a hair wax or gel, a hair spray, a hair foam, a straightener or the like, which can be mixed individually from known components analogously to what is described above for the care agent, the coloring agent and the permanent wave agents.

In various embodiments, the styling agent can be composed so that, despite a reliable styling effect, a (further) hair damage is minimized.

In various embodiments, the system can be extended by further elements, for example, a further analysis device for the hair condition, in particular a hair status, for example, a photometer/colorimeter or a color chart, and/or to a further mixing machine for an individualized hair treatment agent, for example, a hair coloring agent.

In various embodiments, when determining the composition of the hair treatment agent (for example, the hair care/hair coloring agent and/or hairstyling agent), data and/or empirical values of (further) users which can have a similar hair condition (for example, a similar degree of damage and/or a similar hair color) and possibly a similar profile (age, gender, lifestyle habits, hair type, ethnicity, etc.) are considered. A broad set of data and/or experience can be used to optimize the result. In a cloud-based embodiment of the method, the hairdresser can access data and/or experiences of further users who have not necessarily been treated by him and/or are customers of his salon. The system can optionally be designed as a learning system.

In various embodiments, the hair treatment agent can be provided without the user (for example, regularly) being a customer of a hairdresser/salon.

In various embodiments, a standardized and objective assessment of the treatment result can be enabled by employing the system, for example, by employing the sensor device in conjunction with the data processing device. For this purpose, the hair condition of the user after the treatment with the prepared hair treatment agent can be determined by employing the at least one sensor of the sensor device.

In various embodiments, the system for providing the hair treatment agent can be configured in such a way that a determining of a degree of the most important, namely the oxidative hair damage, for example, by a determining of a content of cysteic acid, can be determined exactly by employing the sensor device. The sensor in this case can be at least one optical sensor, which can be configured to record one or more images in a fluorescence region and/or in a near-infrared region (NIR region).

The fluorescence region can, in various embodiments, be a wavelength range in which damaged hair emits autofluorescence and/or a wavelength range in which fluorescent dyes which are more strongly adsorbed by damaged hair than by undamaged hair emit fluorescent light.

The near-infrared region may, in various embodiments, be a wavelength range in which damaged hair has absorption structures, for example, in which cysteic acid absorbs light. Detection takes place in the near-infrared (780-2500 nm or ca. 12,800-4,000 $cm^{-1}$) in near-infrared spectroscopy. Hereinafter, the term near-infrared (NIR) is used for light having a wave number in a range of from about 12,800 to about 4,000 $cm^{-1}$ and the term infrared (IR) is used for light having a wavenumber in a range of from about 3999 to about 400 $cm^{-1}$.

Undamaged hair can typically have a cysteic acid content in a range of from about 0.5% to about 1% (by weight). In the presence of damage, for example, as a result of multiple ultra-bleaching and/or other damage mechanisms, the cysteic acid content can increase to over about 15% (wt).

In various embodiments, this property is used to quantify the degree of damage of the hair as a content of cysteic acid.

In various embodiments, damaged hair can show autofluorescence, which is used to determine the degree of damage by detecting a fluorescence intensity of the hair.

In various embodiments, the hair can be wet with a fluorescent dye solution which is better adsorbed by damaged hair than by undamaged hair, wherein the fluorescent dye solution can have rhodamine B, coumarin, and/or fluorescein.

In various embodiments, the hair can be exposed to UV light (for example, light in a wavelength range of from about 315 nm to about 380 nm) to determine the fluorescence intensity of the hair. The sensor device can be provided with a UV light source for this purpose. The UV light source can be a UV LED or another suitable light source, for example, a conventional UV lamp as used in bill validation.

Fluorescent light emitted from the hair can be registered during the exposure. The fluorescence intensity can be determined from the registered light. The degree of damage to the hair can then be determined taking into account the fluorescence intensity of the hair.

Accordingly, in various embodiments, the sensor device can have an optical sensor which is sensitive at least in the fluorescence wavelength range, for example, a camera, a photometer, a colorimeter and/or a spectrometer. In various embodiments, a filter can be arranged between the hair and the optical sensor in various embodiments.

In various embodiments, the near-infrared (NIR) and/or infrared (IR) spectrum can be obtained, for example, by ATR (near-infrared) spectroscopy ("attenuated total reflection"). By applying mathematical models, a mathematical model can be created by measuring calibration hair samples which have a cysteic acid content determined based on a known analytical method.

In an analysis of an NIR or IR spectrum recorded on the hair of the consumer, or at least a part thereof, in various embodiments, the model can allow a calculation of the content of cysteic acid, and thus the hair damage. An analysis of at least part of the spectrum and an application of the model can be executed in this case by employing the data processing device, for example, (with suitable apps) by employing known smartphones, tablets or the like.

The sensor device can have an NIR light source or/and an IR light source for exposing the hair to NIR or IR light.

Determining the degree of damage to hair according to various embodiments can be performed using either the near-infrared region, that is, by irradiating the hair with the near-infrared light and spectral analysis of at least a part of the NIR light after it has interacted with the hair, or using the infrared region, that is, by irradiating the hair with infrared light and spectral analysis of at least a part of the IR light after it has interacted with the hair, or using both the near-infrared and the infrared region, that is, by irradiating the hair with near-infrared and infrared light and spectral analysis of at least a part of the NIR and at least a part of the IR light after it has interacted with the hair.

In various embodiments, a measured near-infrared (NIR) region can have wavenumbers of from about 12,800 $cm^{-1}$ to about 4,000 $cm^{-1}$, for example, from about 5022 $cm^{-1}$ to about 4020 $cm^{-1}$. This wavelength range can have characteristic overtone and combination vibrations of, for example, CH, OH and NH groups.

In various embodiments, the at least a part of the near-infrared and/or infrared light can have an (infrared) wavenumber range of from about 1100 $cm^{-1}$ to about 1000 $cm^{-1}$, for example, about 1040 $cm^{-1}$. The relevant absorption bands of the component cysteic acid to be analyzed can be found here, among other things.

In various embodiments, based on results of a quantitative computer-assisted evaluation (also referred to as chemometric analysis) for a plurality of calibration hair samples in combination with an independent method, for example, by employing high pressure liquid chromatography, a calibration model can be created for the same calibration hair samples obtained values for a cysteic acid content of the respective calibration hair sample.

If the calibration model is present, in various embodiments, it can be very easy to calculate the concentration of cysteic acid (as a measure of hair damage) from the spectra in comparison to the calibration spectra for the hair to be measured on the basis of the recorded (N)IR spectrum.

Likewise, for other hair ingredients, such as amino acids, lipids, water or melamine, a calibration model can be created and for the hair to be measured, on the basis of the recorded (N)IR spectrum, the concentration of the hair ingredient can be calculated to determine hair status from the spectra compared to the calibration spectra.

In various embodiments, the determining of the hair condition, in particular the degree of damage, of the hair can have a determining of a surface damage of the hair by employing interference reflection microscopy.

Very thin hair structures can be examined with the help of interference reflection microscopy. Interference microscopy is based on the formation of interference that occurs when light is reflected at the top and bottom interfaces of a structure, and reflected light from both interfaces interferes with each other. This results in interference patterns that can be observed, providing information about the thickness of the structure. The resulting interference colors permit structural measurements in the range below 200 nm. These structural measurements can be assigned corresponding to microscopically recognizable structures by viewing the interference colors through a light microscope.

According to various embodiments, this can be applied to the cuticle of hair to determine the degree of damage to the hair.

In this case, light emitted by the hair during an exposure of the hair can be registered. Based on the registered light, first regions of the hair can be detected which reflect the light with higher interference and therefore appear brighter in a recording of the light, and second regions of the hair which reflect the light with lower interference and therefore appear darker. The degree of damage of the hair can be determined based on the sizes of the first regions and the second regions.

The hair has a cuticle, a cortex and medulla.

When the hair is irradiated with light (for example, white light) which can be provided by a light source of the sensor device, for example, a white light LED, a part of the light is reflected on the outer surface of the cuticle and a part is reflected at the interface between cuticle and cortex (in particular when the cuticle has lifted off or detached from the cortex, which typically corresponds to damage to the hair). The reflected parts interfere and form an interference pattern.

The sensor device can have a camera which can be coupled to an interference microscope of the sensor device. The interference microscope, which can have a magnification factor in a range of from about 10-1000, for example, from about 200-400, can be directed to the hair and image the light reflected from the hair, for example, from one or more hair fibers, onto a detector of the camera, which can register the reflected light as at least one (digital) photo.

The data processing device can determine the type and/or number of interference patterns of the hair by employing image analysis software in various embodiments for the or each of the photos, compare them with a calibration model created in the same way and thus determine a degree of damage of the hair. In the case of a plurality of photos, the data processing device can, for example, form an average value of the degrees of damage determined for the photos.

The interference microscope, the camera, the data processing device and optionally also the light source can be realized in various embodiments by a smartphone that is equipped with a microscope lens for smartphones, which is also suitable for interference microscopy. In order to ensure stable examination conditions, the hair can be arranged on a support in various embodiments. This can be provided for example, by employing the data processing device (for example, the smartphone) or an attachment for the data processing device.

For example, hair can be recorded at about 350× magnification by employing a portable electronic device (such as a smartphone, a tablet, etc.) with a microscope attachment (such as a Scrona µpeek) in combination with an interference slider such as offered by Hirox Ltd.

The surface part of the interfering hair structures, that is, the proportion of light (damaged) areas to the total region of the hair in the photograph, lies, for example, between about 1% and about 50%, for example, between about 5% and about 30%.

The data processing device can then deduce the degree of damage from the determined surface proportion of bright areas, for example, with the aid of a table which assigns ranges of area proportions to degrees of damage.

One type of damage, which can be determined by employing interference reflection microscopy, can be, for example, mechanical damage, such as can be caused by stretching of the hair, for example.

In various embodiments, suitable mathematical models of predictive analytics can be used for the quantification of the cysteic acid content (for example, by employing fluorescence analysis and/or (N)IR spectroscopy) or the degree of damage (for example, by employing (N)IR spectroscopy, by employing interference reflection microscopy and/or by employing acoustic analysis).

In various embodiments, a method of providing a hair treatment agent is provided which is simple in use and which enables a precise determining of a hair condition, in particular a degree of (oxidative) damage to hair or a hair condition with the aid of fluorescence detection and/or by detection of absorption and/or by detection of surface damage of the hair and methods of predictive analytics.

In various embodiments, the determining of the hair condition can, due to its ease of experimental feasibility, be suitable for execution using a portable data processing device, also referred to as a mobile data processing device. A smartphone, an iPad, a tablet or laptop can be used as a portable data processing device.

In various embodiments, a method can be provided which makes it possible, by employing simple image analysis methods, which can be realized, for example, to provide an individualized hair treatment agent using a mobile data processing device (for example, a smartphone), a few further simple devices (for example, a UV LED, a white light, an NIR and/or IR light emitting device, a filter, a portable NIR sensor, a portable (NIR and/or VIS) spectrometer, a microphone comb, and/or a microscope) and a predictive analytic method.

In various embodiments, the individualized hair treatment agent can be suitable for achieving a desired effect (for example, hair color, hair care condition, hair status, and/or hair styling).

In various embodiments, an intensity of absorption of the (N)IR light by a hair ingredient, in particular by water or cysteic acid, or an intensity of fluorescent light can be easily detected under standardized conditions with the aid of image analysis methods. By applying mathematical models in the field of predictive analytics, a mathematical model can be created by measuring standard hair samples which have a content of hair ingredients determined on the basis of known elaborate methods, which then allows a calculation of the hair ingredient, in particular cysteic acid or water, and thus the hair damage and/or the hair status in the hair of the consumer based on the registered (N)IR absorption or the registered fluorescent light and the fluorescence intensity determined therefrom. The image analysis can, for example, (using suitable apps) be performed by employing known smartphones, tablets, etc.

In various embodiments, the use of mathematical models in the field of predictive analytics (such as tree ensembles, neural networks or support vector machines) allows a much more accurate calculation of the hair condition, in particular the hair damage and/or the hair status (which form a dependent variable in the models), as would be possible with simple models, for example, a simple linear regression. The methods in this case can use a variety of input variables in parallel and also map non-linear relationships. For example, in various embodiments, these models enable inclusion of categorical, non-metric input variables, such as a hair color (for example, blond, brown, black, etc.) and/or ethnicity of a hair type (for example, Caucasian, Asian, Afro-American), which can have an influence on a resulting fluorescence intensity. The input variables can be detected in various embodiments by employing the sensor device, for example, the hair color using a camera (for example, the smartphone camera), a colorimeter or a color chart, the hair type using the camera.

In various embodiments, a camera recording of the hair can be used to determine, by employing image analysis methods, not only the hair color, but in addition, a hair structure. The ethnicity, for example, black/curly: Afro-American, black-smooth: Asian, etc.) can be determined based on a combination of hair color and hair structure.

According to various embodiments, the plurality of NIR absorption-influencing or fluorescence intensity-influencing parameters can have a hair color and/or an ethnicity of a type of the hair.

According to various embodiments, the predictive analytics can use at least one method from a group of methods, wherein the group of methods has:
linear or multi-linear regression, polynomial regression, neural-network methods, support vector machine methods, decision tree methods ("decision trees", "random forest", "tree ensembles") and further methods.

In various embodiments, the external hair damage can be determined by employing a sensor device which has a sensor for detecting acoustic emissions, for example, a microphone, for example, by employing a contact microphone comb.

Herein, the sensor for detecting acoustic emissions for the sake of simplicity can also be referred to as a microphone. However, unless otherwise stated and suitable for the described function, the sensor for detecting acoustic emissions can also be, for example, an acceleration sensor (which can be suitable for detecting accelerations due to acoustic emissions in a certain frequency range) or the like.

The sensor device can be executed in various embodiments as a contact microphone comb. The contact microphone comb can, in various embodiments, have a substantially commercial hair comb to which one or more externally attached measuring systems for acoustic emission (that is, sound emissions; a Korg contact microphone can be used as an exemplary measuring system for acoustic emissions) and/or acoustic emission measuring probes are connected.

In various embodiments, signals of generated sound or vibration, which arise when combing through hair of a user, can be recorded by employing the sensor device having the microphone.

In various embodiments, the sensor device can have one or more acoustic emission measuring systems and/or probes, for example, one or more contact microphones and/or an acceleration sensor. The sensor device can further have, in various embodiments, an internal or external amplifier for amplifying signals measured by employing the measuring system for acoustic emission.

In various embodiments, an analysis of hair damage can be provided by digitizing information from a microphone (and at least one further sensor) and providing that data on a cloud platform.

The information can be provided after processing for comparison with already recorded examples (reference data). A degree of hair damage can be known for the reference data, such that as a result of the comparison, for example, the degree of hair damage of the most similar reference data can be provided as a result in digital form, for example, transmitted back.

By using various sensors such as lenses, gyroscopes and accelerometers, it can be possible to determine a position of the sensor device, for example, a position in a person's hand, to determine a suitable cosmetic hair care (for example, products) and to prevent unnecessary hair damage, for example, hair loss. For example, an acceleration sensor can be used to determine a beginning and/or an end of a detection process. Assuming that a detection process typically begins at the hairline and ends at the hair tips, optionally, a spatially resolved determination, for example, hairline/mid-region/tips, of the hair condition information, hair color and associated hair damage can be enabled in combination with a speed determined by employing the acceleration sensor with which speed the portable sensor device is moved. Also, an acceleration sensor or a gyroscope can be used to ensure the reliability of a detection process with an optical sensor, in which, for example, the user receives an audible and/or visual warning signal at too high a forward movement speed of the portable sensor device during the detection process.

In the context of this application, the acceleration sensor feature can comprise a "classical" motion sensor or a gyroscopic sensor.

The data transmission of the sensor device to the data processing device can take place in various embodiments by employing cables or via known radio data transmission standards (for example, Bluetooth, WLAN, NFC, Thread, ZigBee, etc.).

In various embodiments, a device for providing a hair treatment agent is provided. The device can have at least one portable sensor for the detecting of at least one sensor value on hair of a user, a data processing device for the determining of a hair condition of the user by employing the detected at least one sensor value and for the computer-assisted determining of a user-specific hair treatment agent including the determined hair condition, and a hair treatment agent mixing device for preparing the determined user-specific hair treatment agent.

In various embodiments, the determining of the hair condition can have at least a determining of a degree of damage to the hair.

In various embodiments, the determining of the hair condition can have at least a determining of a hair condition.

In various embodiments, the at least one sensor can have at least one optical sensor for the determining of a hair ingredient content, in particular a cysteic acid content of the hair, and/or for the determining of a hair color of the user and/or for the determining of a mechanically induced damage to the hair.

In various embodiments, the at least one sensor can have a microphone for the detecting of a surface roughness of the hair.

In various embodiments, the data processing device can be part of a smartphone, a tablet or a smart mirror.

In various embodiments, the hair treatment agent mixing device can have a mixing device for producing a hair care agent, a hair coloring agent and/or a hair styling agent. A hair coloring agent is understood to mean an agent of changing a hair color. Thus, the hair coloring agent can either be a coloring to create a hair color (for example, black, brown or red), or a bleaching agent to lighten/remove a hair color by destroying the melanins.

In various embodiments, the sensor device and the data processing device can form an integrated device.

In various embodiments, the data processing device and the hair treatment agent mixing device can form an integrated device.

In various embodiments, the at least one sensor and/or the data processing device can have a device for wireless data transmission.

In various embodiments, the device can have a UV lamp for exposing the hair to UV light, wherein the at least one sensor can have a device for registering fluorescent light emitted from the hair. The fluorescent light can be an autofluorescence of the damaged hair, and/or a fluorescence of fluorescent dye adsorbed in the hair sample. The hair may have been removed from the head, for example, to wet the hair with a fluorescent dye solution and/or to register the fluorescent light, or the hair can remain on the head of the user, for example, when registering the autofluorescence of the hair.

In various embodiments, the determining of the hair condition can have a computer-assisted determining of treatment results achievable by employing a plurality of hair treatment agents by employing predictive analytics including the determined hair condition and a selecting of the user-specific hair treatment agent based on the determined treatment results.

In various embodiments, a method for providing a hair treatment agent by employing a device for the determining of the hair treatment agent is provided. The method can have a detecting of at least one sensor value of hair of a user by employing at least one portable sensor, a determining of a hair condition of the user by employing the detected at least one sensor value, wherein the determining of the hair condition has at least a determining of a degree of damage to the hair and/or a hair status, a computer-assisted determining of a user-specific hair treatment agent including the determined hair condition, and a preparation of the determined user-specific hair treatment agent by employing a hair treatment agent mixing device.

In various embodiments, the determining of the degree of damage of the hair can have a determining of a cysteic acid content of the hair.

In various embodiments, the determining of the cysteic acid content of the hair can have a determining of a fluorescence intensity.

In various embodiments, the determining of the cysteic acid content of the hair can have a determining of an absorption intensity, for example, in an NIR spectral region.

In various embodiments, the determining of the hair condition can have a determining of a content of a hair ingredient.

In various embodiments, the determining of a content of a hair ingredient can have a determining of a content of an amino acid, a lipid, a melanin, and/or water.

In various embodiments, the determining of the content of an ingredient of the hair can have a determining of an absorption intensity, for example, in a VIS, NIR, and/or IR spectral range.

In various embodiments, the determining of the degree of damage of the hair can have a determining of a surface roughness of the hair.

In various embodiments, the determining of the degree of damage of the hair can have a determining of a surface damage of the hair by employing interference microscopy.

In various embodiments, the determining of a hair status can have a determining of a hair color of the user.

In various embodiments, the method can further have providing a treatment goal by the user.

In various embodiments, the treatment agent can have a hair coloring agent, a hair care agent and/or a hair styling agent.

In various embodiments, the method can further have transmitting the detected sensor value from the sensor to a data processing device and/or transmitting the determined hair treatment agent from the data processing device to the hair treatment agent mixing device.

The determined treatment results can be displayed by employing a display device in various embodiments.

In the following detailed description, reference is made to the accompanying drawings which form a part of the present application and in which is shown by way of illustration specific embodiments in which the present disclosure can be practiced. It should be understood that other embodiments can be utilized and structural or logical changes can be made without departing from the scope of the present disclosure. It should be understood that the features of the various embodiments described herein can be combined with each other unless specifically stated otherwise. The following detailed description is therefore not to be taken in a limiting sense, and the scope of the present disclosure is defined by the appended claims.

In the present description, the terms predictive analytics, big data and data mining are used interchangeably.

In the case of a smartphone referred to herein, unless otherwise stated in the context, this is to be understood as representative of all similar portable data processing devices, that is, smartphones, tablets, iPads, laptops, etc. The same applies to smartphone cameras and the like.

A hair coloring agent is understood to mean an agent for changing a hair color. Thus, the hair coloring agent can either be a coloring to produce a hair color (for example, black, brown or red), or a bleaching agent to remove/lighten a hair color.

FIGS. 1, 2A to 2K, 3A to 3M and 4A to 4K each show a schematic illustration of a device 100 for providing a hair treatment agent according to various embodiments.

Different embodiments of the device 100 for providing the hair treatment agent and other devices (sensor device 110, data processing device 116, hair treatment agent mixing device 120) are marked with trailing letters and optionally numbers.

In various embodiments, the device 100 can have a portable sensor device 108 having at least one sensor 110 for the detecting of at least one sensor value on hair of a user, a data processing device 116 for the determining of a hair condition of the user by employing the detected at least one sensor value, wherein the determining of the hair condition has at least a determining of a degree of damage of the hair or determining of a hair status, and for the computer-assisted determining of a user-specific hair treatment agent including the determined hair condition, and a hair treatment agent mixing device 120 for preparing the determined user-specific hair treatment agent.

In various embodiments, the at least one sensor 110 can have, as illustrated in FIGS. 1, 2B, 2D, 2E, 2G, 2J, 2K, 3B, 3D, 3F, 3G, 3J, 3L, 3M, 4B, 4D, E, 4G, 4J and 4K, at least one optical sensor 110*b*, 110*c*, 110*e* respectively.

The at least one optical sensor 110*b*, 110*c*, 110*e* can have, in various embodiments, as illustrated in FIGS. 1, 2E, 2J, 2K, 3G, 3L, 3M, 4E, 4J and 4K, an optical sensor 110*c*, 110*e* for the determining of a hair ingredient content, in particular a cysteic acid content, of the hair and/or for the determining of a hair color of the user.

An optical sensor herein is understood to mean a sensor which, by employing optical elements, directs light in a further sense (UV light, visible light (also abbreviated to VIS), near-infrared light (NIR) and/or infrared light (IR)) and, by employing a detector (for example, an electronic detector, for example, for visible light, for NIR and/or IR light, a photometer or the like) detects light.

As described above, the optical sensor 110*e* for the determining of a hair ingredient content, in particular a cysteic acid content, of the hair can, in various embodiments, have a camera and/or a spectrometer for detecting light in a wavelength range of visible light, wherein the light is radiated as fluorescent light from the hair when exposed to ultraviolet light.

In various embodiments, a single optical sensor can be configured in the optical sensor 110*e* in such a way that only the fluorescent light can be detected for evaluation, for example, in a case where at least one filter is arranged between the hair and the optical sensor, which or by which allows at least one only or mainly a wavelength range of the fluorescent light to pass.

If it is provided to additionally detect the hair color by employing the sensor device 108 in such a case, the filter can be configured to be removable, for example, as a filter attachment for a smartphone camera, so that the detecting of the fluorescent light and a detecting of visible light in several wavelength ranges (for example, R, G, B) can be performed sequentially to determine the hair color. Alternatively, the filter can have a plurality of regions, for example, a bandpass region for the fluorescent light, possibly a bandpass region outside the fluorescent light wavelength region and/or a substantially unfiltered region. Alternatively, the at least one optical sensor 110*e* can have a plurality of optical sensors 110*e*, wherein at least one of the sensors is used for the detecting of the fluorescent light, and a further of the sensors is arranged for the determining of the hair color, for example, as a camera, for example, a camera of a smartphone, tablet, etc., or for example, as a spectrometer.

In various embodiments, a single optical sensor can be configured in the optical sensor 110*e* in such a way that both the fluorescent light can be detected for evaluation and a determining of the hair color of the user is made possible, for example, when the optical sensor 110*e* is designed as a spectrometer.

The optical sensor 110*c* for the determining of a hair content, in particular a cysteic acid content, of the hair can, as described above, in various embodiments, have an (N)IR camera and/or an (N)IR spectrometer for detecting light in a wavelength range, in which the hair ingredient, in particular cysteic acid, absorbs light.

If it is provided to additionally detect the hair color in such a case by employing the sensor device 108, the at least one optical sensor 110*c*, 110*e* can have a plurality of optical sensors 110*c*, 110*e*, wherein at least one of the sensors 110*c* for the detecting of the (N)IR light is used, and a further of the sensors is configured 110*e* for the detecting of the visible light for the determining of the hair color. Alternatively, the optical sensor 110*c* can be a sensor for detecting visible light and (N)IR light.

In various embodiments, the optical sensor 110*e* can be configured only to detect a hair status, in particular the hair color, and the hair damage can be detected by employing another, for example, acoustic, sensor.

In various embodiments, the at least one sensor 110 can have, as illustrated in FIGS. 1, 2B, 2D, 2E, 2G, 2J, 2K, 3B, 3D, 3F, 3G, 3J, 3L, 3M, 4B, 4D, E, 4G, 4J and 4K, at least one optical sensor 110*b* for the determining of a mechanically induced damage to the hair (and possibly to determine a hair status, in particular a hair color, of the user).

As described above, the mechanically induced hair damage can be determined by employing interference reflection microscopy, for which purpose the microscope 110*b* can be provided in various embodiments.

In various embodiments, as described above, the microscope 110*b* can be designed as a microscope attachment for a camera, for example, for a smartphone camera. Accordingly, the attachment can be removable, and the smartphone camera can then be useful for the determining of the hair color and/or for detecting fluorescent light or (N)IR light.

In various embodiments, the microscope 110*b* can be designed as a separate sensor device 108 or as part of a sensor device 108, which can have further sensors 110, for example.

Figure 2C:
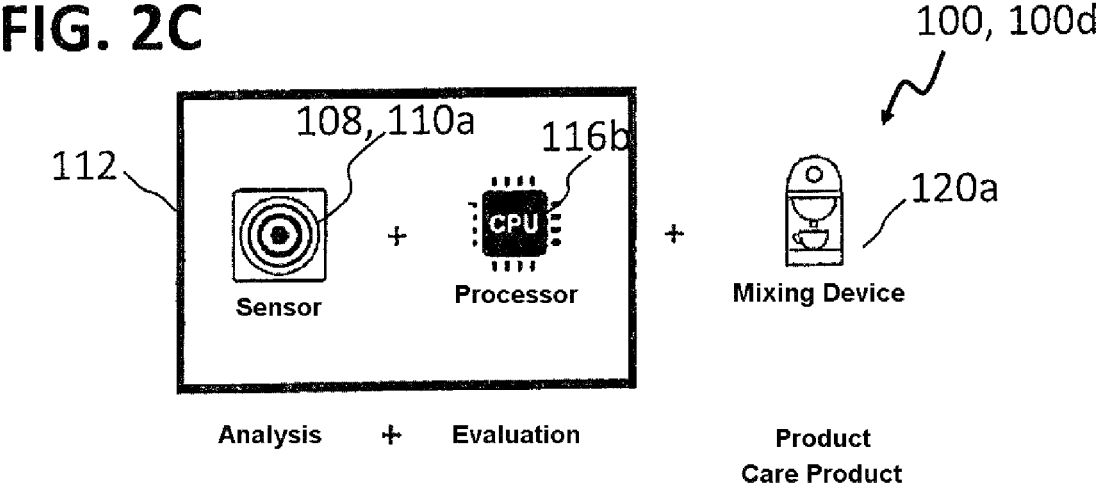
Figure 2D:
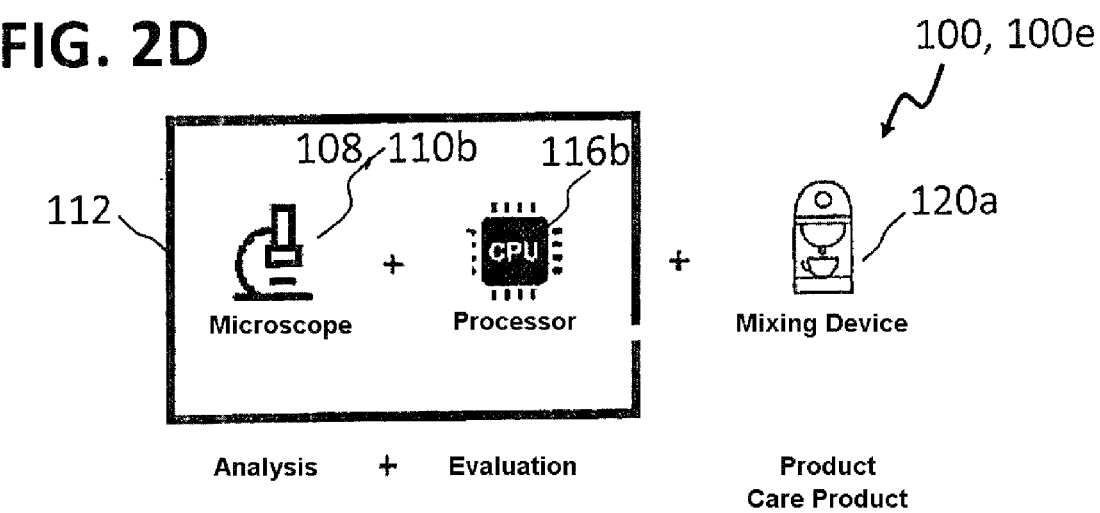
Figure 2E:
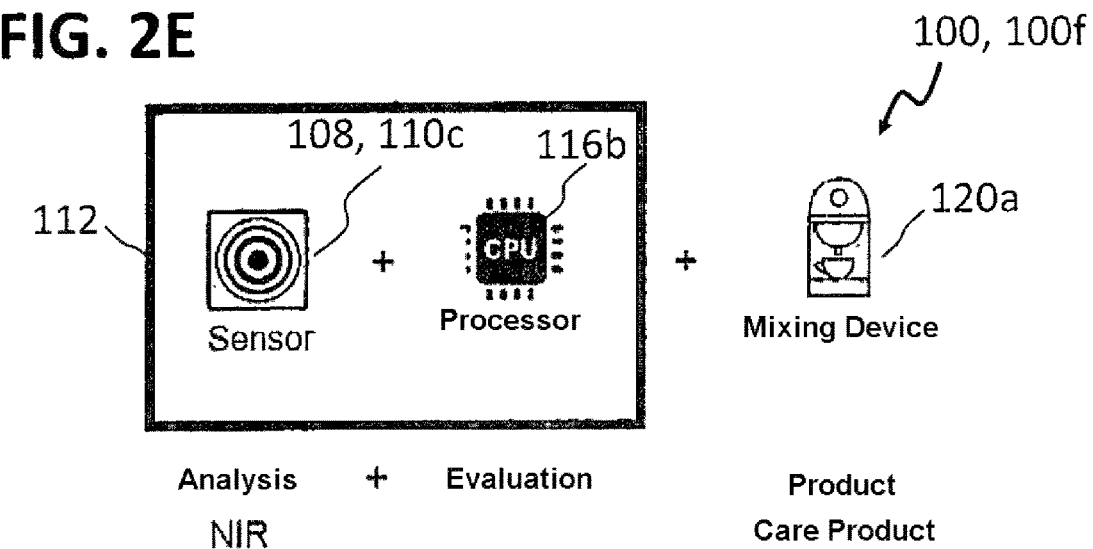
Figure 2F:
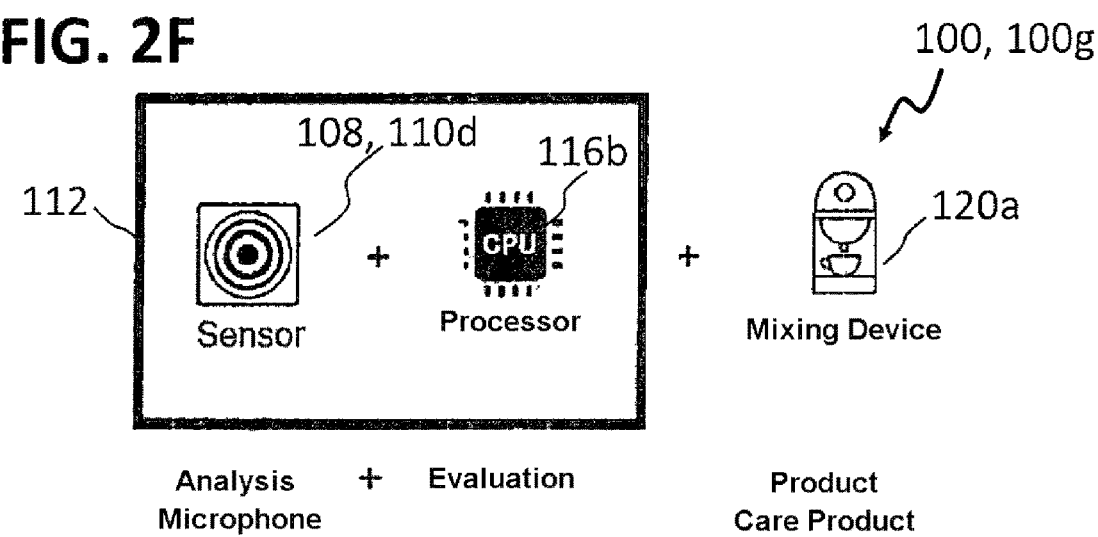
Figure 3A:
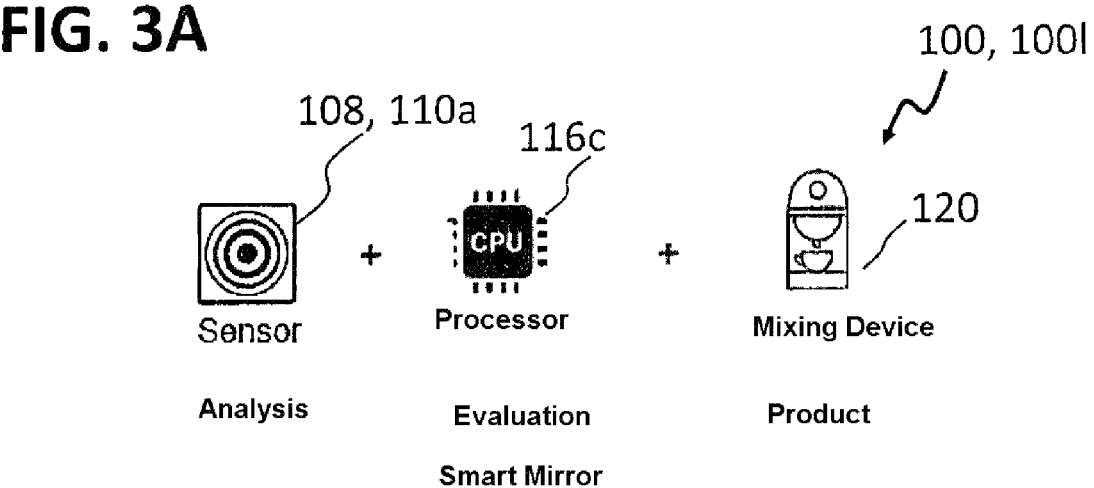
Figure 3B:
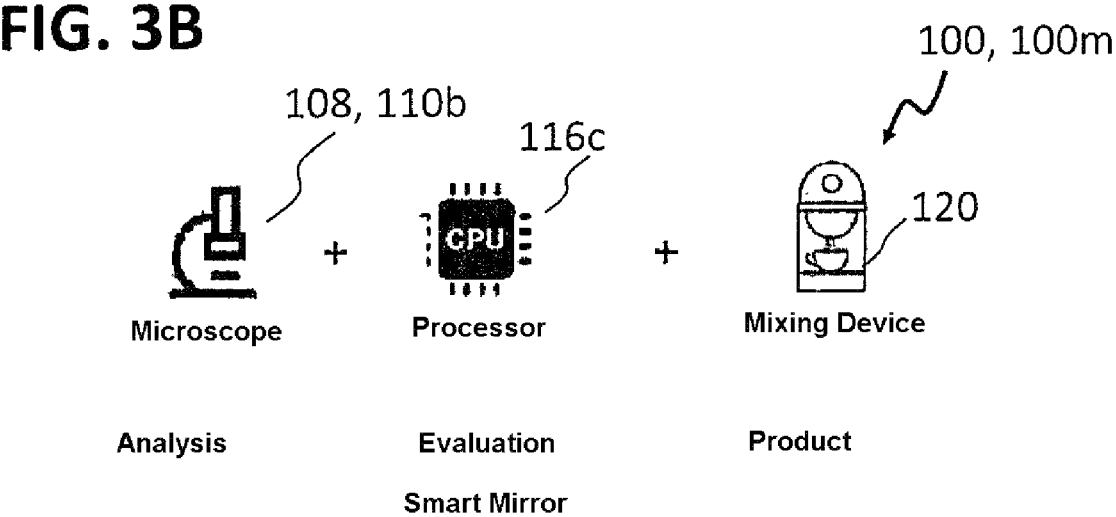
Figure 3C:
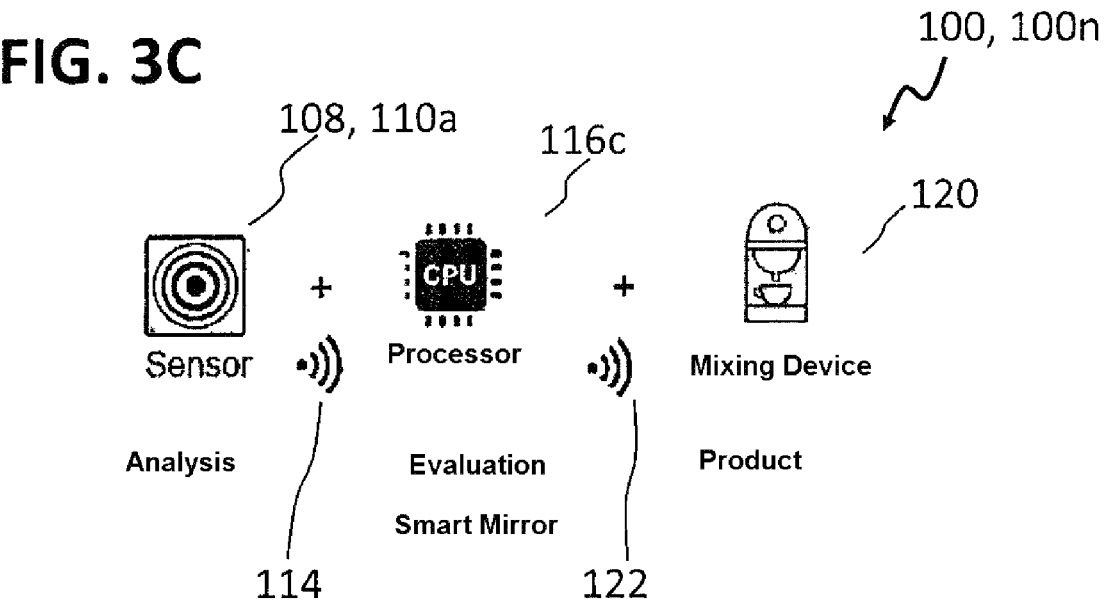
Figure 3D:
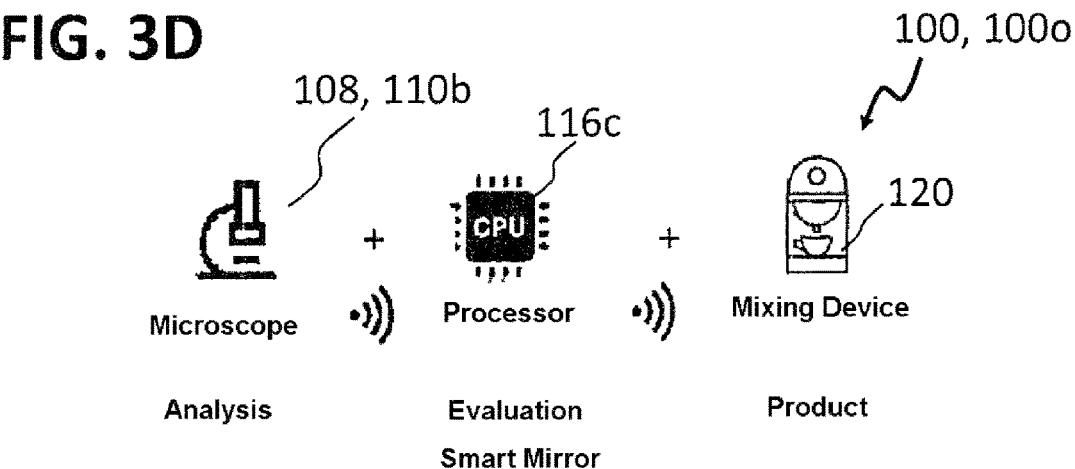
Figure 3E:
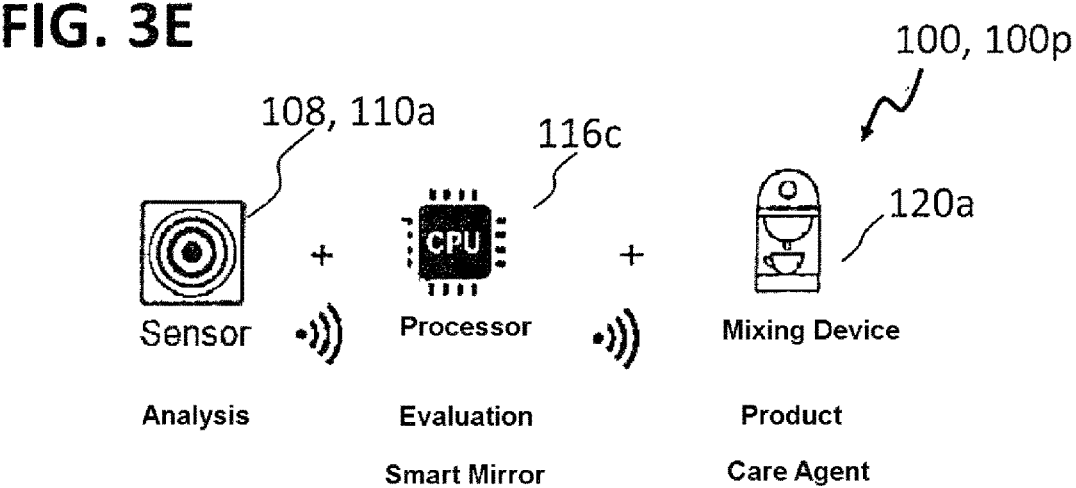
Figure 3F:
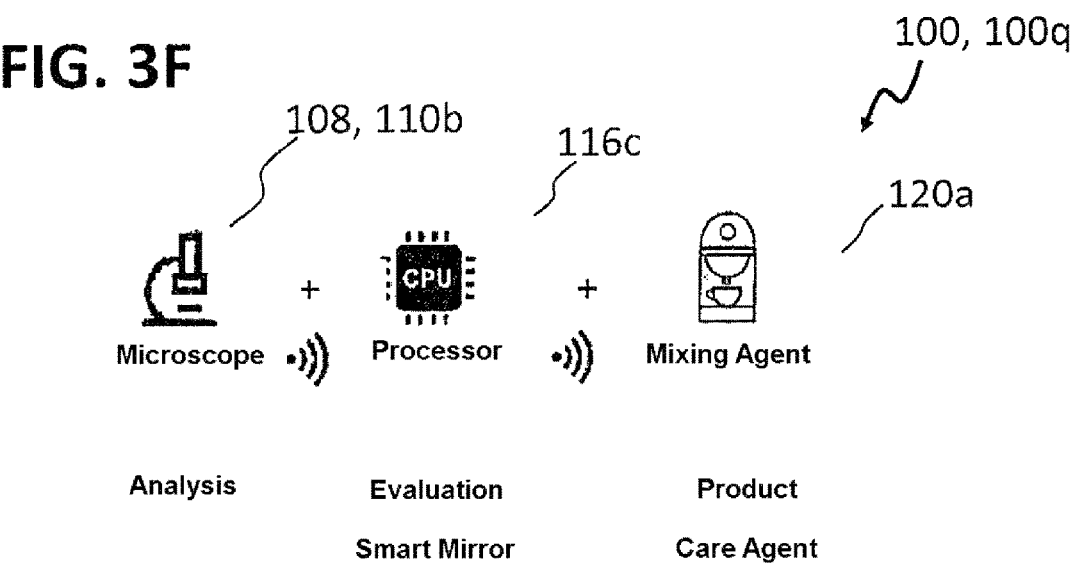
Figure 3G:
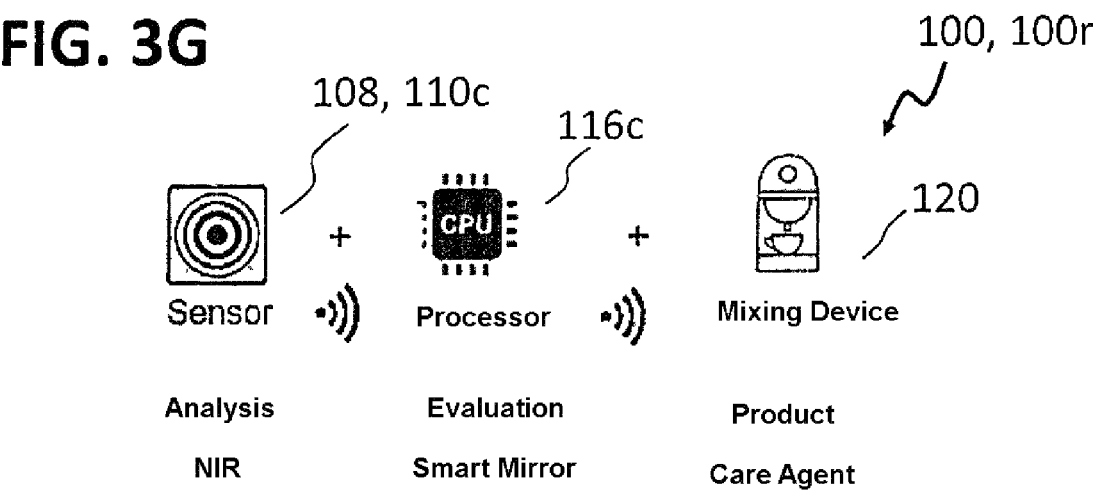
Figure 3H:
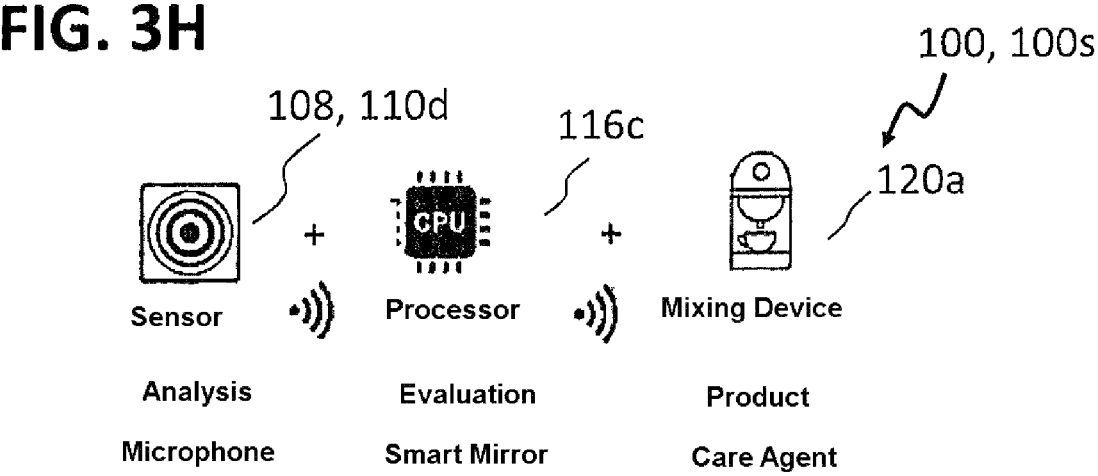

In various embodiments, the at least one sensor 110 can have, as illustrated in FIGS. 2F, 3H and 4F, at least one microphone 110*d* for the detecting of a surface roughness of the hair. The surface roughness of the hair can be determined in various embodiments as described above by employing the microphone 110*d*.

The degree of damage of the hair can be determined on the basis of the determined surface roughness in various embodiments, for example, as described above.

In various embodiments, the registered light and/or the registered noise or possibly another or further detected sensor value can be transferred to the data processing device 116 as raw data and/or in processed form, for example, as a digital photograph or another quantification of the registered light, as an audio file, Fourier transformation etc. This is, in order to not affect a clarity of the figures, only designated in FIG. 1C3 by way of example by the reference numeral 114. However, even in the other embodiments, the detected sensor values can be supplied in raw and/or processed form to the data processing device 116.

Transmission can take place using known methods and devices, for example, a data cable, wireless data transmission (for example, Bluetooth, WLAN, ZigBee, Thread, or Near Field Communication (NFC)), or transmission can take place when the sensor device 108 forms the integrated device 112 with the data processing device 116 as described above (for example, when using the camera and/or the microphone of a mobile phone, tablet, laptop or the like as a camera).

In various embodiments, the sensor device 108 can be designed as a comb or brush. In other words, the at least one sensor 110 can be integrated into a comb- or brush-shaped body.

In various embodiments, in particular, the microphone 110d can be integrated into the comb- or brush-shaped body, for example, as described above.

In various embodiments, one or more sensors 110, for example, one of the optical sensors 110b, 110c, and/or 110e can alternatively or additionally be integrated into the comb- or brush-shaped body.

In various embodiments, the sensor device 108 can, if appropriate, have a body of substantially any desired shape.

In various embodiments, the data processing device 116 can be part of a smartphone, tablet, iPad, etc. or, as illustrated in FIG. 1C1 to 1C12, be part of a smart mirror 116c.

In various embodiments, the hair treatment agent mixing device 120 can have a mixing device 120a for producing a hair care agent, a mixing device 120b for producing a hair coloring agent and/or a mixing device 120 for producing a hair styling agent.

In various embodiments, as illustrated in FIG. 2A to FIG. 2K, the sensor device 108 and the data processing device 116 can form an integrated device.

In various embodiments, as illustrated in FIG. 4A to 4K, the data processing device 116 and the hair treatment agent mixing device 116 can form an integrated device 118.

In various embodiments, the sensor device 108 and/or the data processing device 116 can have a device for wireless data transmission, for example, for data transmission by employing WLAN, Bluetooth, ZigBee, Thread, NFC or the like, for example, as described above.

In various embodiments, the device can have a UV lamp for exposing the hair to UV light, wherein the sensor device 108 can have a device for registering fluorescent light emitted from the hair, for example, as described above.

The fluorescent light can be an autofluorescence of the damaged hair, and/or a fluorescence of fluorescent dye adsorbed in the hair sample. The hair may have been removed from the head, for example, to wet the hair with a fluorescent dye solution and/or to register the fluorescent light, or the hair can remain on the user's head, for example, registering the autofluorescence of the hair.

In various embodiments, the determining of the hair condition can have a computer-assisted determining of the degree of hair damage and/or the hair color, for example, by employing predictive analytics.

In various embodiments, the determining of the user-specific hair treatment agent can have a computer-assisted determining of the hair treatment agent, for example, by employing predictive analytics, including the degree of hair damage and/or the hair condition.

The data processing device 116 can be equipped, for example, with corresponding software, for example, an app, for example, as described above for receiving and further processing the data.

In various embodiments, a cysteic acid content can be determined by employing the data processing device 116 on the basis of a measure (for example, of an equivalent width) for the (N)IR absorption or the determined fluorescence intensity. For this purpose, for example, as described above, mathematical models from the field of predictive analytics can be used to determine a relationship between the measure of the (N)IR absorption or the (standardized) fluorescence intensity and an associated cysteic acid content (and thus a degree of damage to the hair).

As independent parameters, the model can in various embodiments include, for example, a relationship between cysteic acid content and (N)IR absorption or cysteic acid content and fluorescence intensity or corresponding data values, for example, in the form of associated data pairs, which were determined or mathematically modeled by measuring standard hair samples, which have a cysteic acid content determined by employing known elaborate methods.

Accordingly, different sensor values can be used in various embodiments in order to determine the degree of damage of the hair and/or the hair status.

In various embodiments, the degree of damage of the hair can be determined in a categorical scale (for example, light, medium, heavy).

In various embodiments, the degree of damage can be determined in a metric scale (for example, percentage of the content of cysteic acid, percentage of areas having higher interference or the like).

As described above, the data processing device 116 can, for example, have a mobile data processing device, for example, a smartphone, a tablet or a laptop, in particular in a case where the portable sensor device 108 forms the integrated device 112 with the data processing device 116.

In various embodiments, the data processing device can be of a different type, for example, a desktop computer integrated with the smart mirror, or any other data processing device 116 that is suitable for storing and providing the data and which is to execute the predictive analytics procedure, thus, for example, any data processing device 116 having sufficiently large data memory and sufficiently powerful processor.

In various embodiments, instead of the predictive analytic method, other, for example, simpler, methods for the determining of the hair condition, for example, the degree of damage or the hair color, and/or for the determining of the user-specific hair treatment agent can be used.

In various embodiments, the formulation for the user-specific hair treatment agent determined by employing the data processing device 116 can be transmitted to the hair treatment agent mixing device 120. This is, in order to not affect a clarity of the figures, only designated in FIG. 3C by way of example by the reference numeral 122.

The transmission can take place in a known way, for example, by employing a data cable, wireless data transmission (for example, Bluetooth, WLAN, ZigBee, Thread or Near Field Communication (NFC)), or a transmission can take place within a device, when the data processing device 116 forms an integrated device 118 with the hair treatment agent mixing device 120, for example, as described above and illustrated in FIG. 4A to FIG. 4K.

In various embodiments, as shown in FIG. 4A to FIG. 4K, the data processing device 116 and the hair treatment agent mixing device 120 can form the integrated device 118, for example, in which a processor of the hair treatment agent mixing device 120 is configured to execute the functions of the data processing device 116, for example, to determine the composition of the hair treatment agent, taking into account the hair condition determined by employing the at least one sensor 110. For example, a processor already present in the hair treatment agent mixing device 120 can be configured to provide the additional functionality, or an additional processor can be integrated into the hair treatment agent mixing device 120 to provide the functionality.

In various embodiments, the data processing device 116 can be configured to indirectly determine the hair condition, for example, the degree of hair damage and/or the hair status, and/or the composition of the hair treatment agent, for example, by transmitting the sensor raw data and/or partially evaluated sensor data and/or of a hair condition to an external data processing device, for example, to a cloud server architecture (in short: cloud), and by receiving a result from the external data processing device (for example, the cloud).

In various embodiments, the device for providing the hair treatment agent can be designed as a learning system, for example, in which the user and/or further users provide the hair condition prior to application of the hair treatment agent and the hair condition after treating the hair with the hair treatment agent of the data processing device 116 (for example, by employing the cloud).

In order to provide the hair condition after the treatment, a determining of the hair condition after the treatment with the hair treatment agent by employing the sensor device 108 in conjunction with the data processing device 116 can be used in various embodiments. In other embodiments, another device can be used to determine the hair condition after treatment, and the determined hair condition can be transmitted to the data processing device 116.

FIG. 1 illustrates a device 100a for providing a hair treatment agent according to various embodiments. The device 100a can have a microscope 110 and a further sensor 110a as sensors 110 of the sensor device 108, wherein the further sensor 110a can have one or more of the other described sensors (optical sensor 110c, 110e, acoustic sensor 110d) or one or more non-described sensors suitable for the determining of a hair condition.

The sensor 110a is also referred to in the following as a generic sensor 110a. The device 100a can have a data processing device 116a, which can have one or more of the data processing devices 116 described, for example, a smartphone, a smart mirror, a desktop computer or the like, or in general a processor with an optical or acoustic input and/or output device, for example, a screen, a touch-sensitive screen, a speaker and/or a microphone. The device 100a can have a mixing device 120, wherein the mixing device 120 can be configured to mix a hair care product, a hair color product and/or a hair styling product (this is also referred to as a generic mixing device 120 in the following).

FIG. 2A to 2K respectively illustrate a device 100b to 100k for providing a hair treatment agent according to various embodiments. In each case, the sensor device 108 and the data processing device 116b can be formed as an integrated device 112.

The device 100b of FIG. 2A has, as an integrated device 112, a generic sensor 110a and a data processing device 116b integrated therewith, and further a generic mixing device 120. The integrated device 112 can have, for example, a brush having at least one sensor 110a, a processor and an optical or acoustic input and/or output device. The mixing device 120 can be separate.

The device 100c of FIG. 2B has, as an integrated device 112, a generic sensor 110a and a data processing device 116b integrated therewith, and further a generic mixing device 120. The integrated device 112 can have, for example, a smart terminal having a microscope (attachment), a processor and an optical or acoustic input and/or output device. The mixing device 120 can be separate.

The device 100d of FIG. 2C has, as an integrated device 112, a generic sensor 110a and a data processing device 116b integrated therewith, and further a mixing device 120a for producing a care agent. The integrated device 112 can have, for example, a brush having the sensor 110a, a processor and an optical or acoustic input and/or output device. The mixing device 120a can be separate.

The device 100e of FIG. 2D has, as an integrated device 112, a generic sensor 110a and a data processing device 116b integrated therewith, and further a mixing device 120a for producing a care agent. The integrated device 112 can have, for example, a smart terminal having a microscope (attachment), a processor and an optical or acoustic input and/or output device. The mixing device 120a can be separate.

The device 100f of FIG. 2E has, as an integrated device 112, an NIR sensor 110c for the determining of the hair damage and/or for the determining of the hair status and a data processing device 116b integrated therewith, and further a mixing device 120a for producing a care agent. The integrated device 112 can have, for example, a brush having the sensor 110c, a processor and an optical or acoustic input and/or output device. The mixing device 120a can be separate. Alternatively, not illustrated, a sensor for detecting fluorescent light can be used instead of the NIR sensor 110c.

The device 100g of FIG. 2F has, as an integrated device 112, a microphone 110d for the determining of the surface roughness and a data processing device 116b integrated therewith, and further a mixing device 120a for producing a care agent. The integrated device 112 can have, for example, a brush having the microphone 110d, a processor and an optical or acoustic input and/or output device. The mixing device 120a can be separate.

Figure 2G:
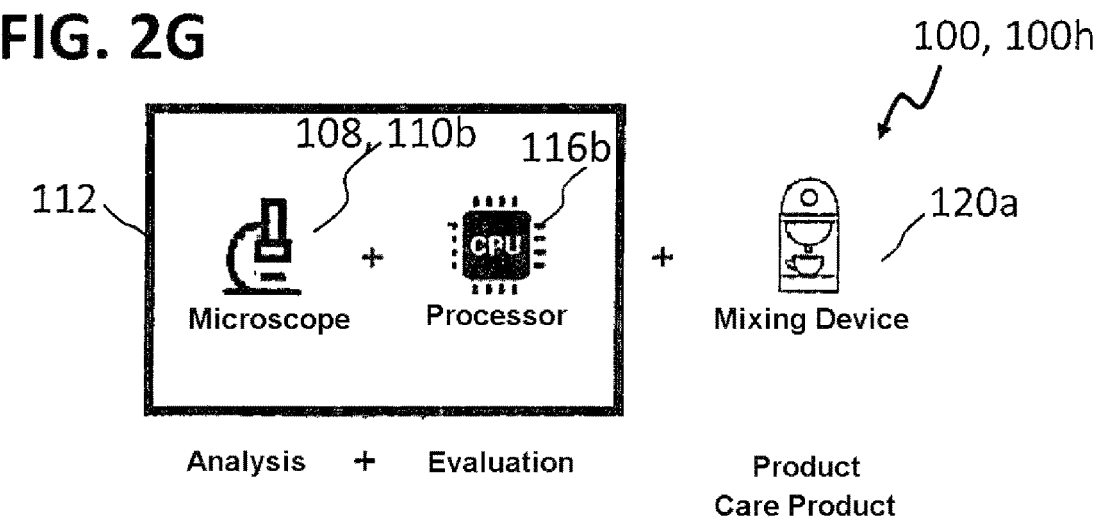

The device 100h of FIG. 2G has, as an integrated device 112, a microscope (attachment) 110b for the determining of the hair damage (for example, stretching damage, for example, by employing image evaluation) and a data processing device 116b integrated therewith, and further a mixing device 120a for producing a care agent. The integrated device 112 can have a processor and an optical or acoustic input and/or output device. The mixing device 120a can be separate.

Figure 2H:
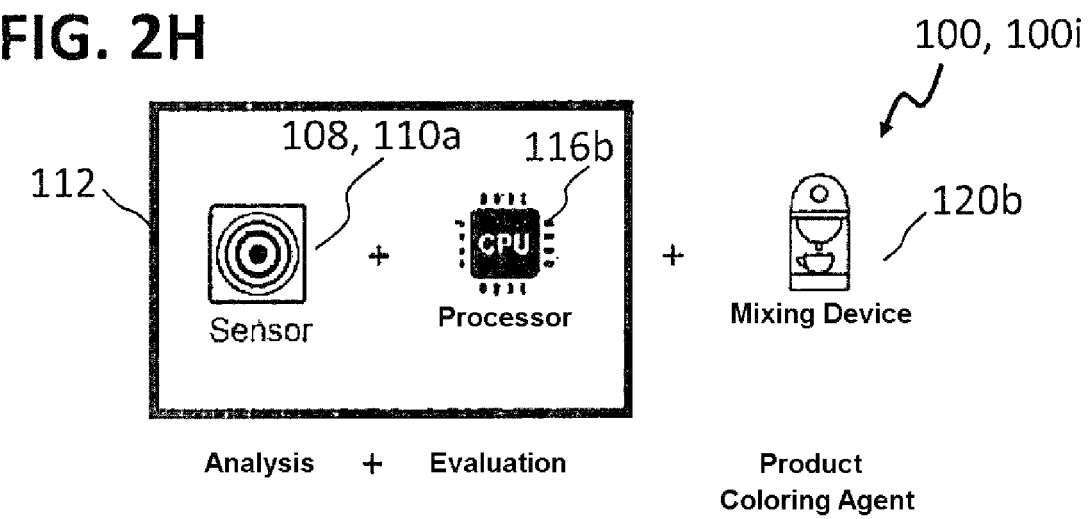

The device 100i of FIG. 2H has, as an integrated device 112, a generic sensor 110a and a data processing device 116b integrated therewith, and further a mixing device 120a for producing a coloring agent. The integrated device 112 can have, for example, a brush having the sensor, a processor and an optical or acoustic input and/or output device. The mixing device 120b can be separate.

Figure 2J:
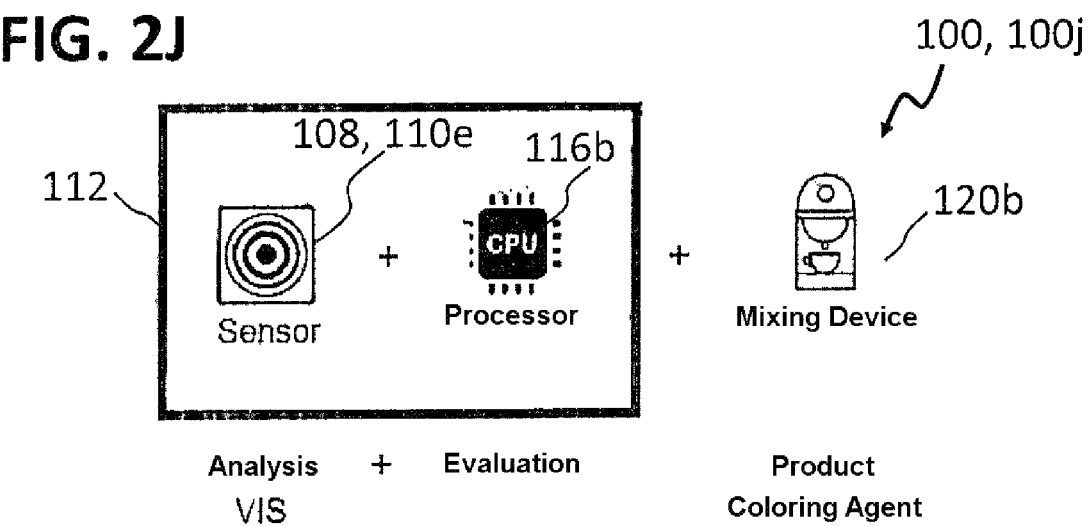

The device 100j of FIG. 2J has, as an integrated device 112, a sensor 110e for visible light the determining of the hair color, for example, a digital color camera or a VIS sensor, and a data processing device 116b integrated therewith, and further a mixing device 120b for producing a coloring agent. The integrated device 112 can have a processor and an optical or acoustic input and/or output device. The mixing device 120b can be separate.

Figure 2K:
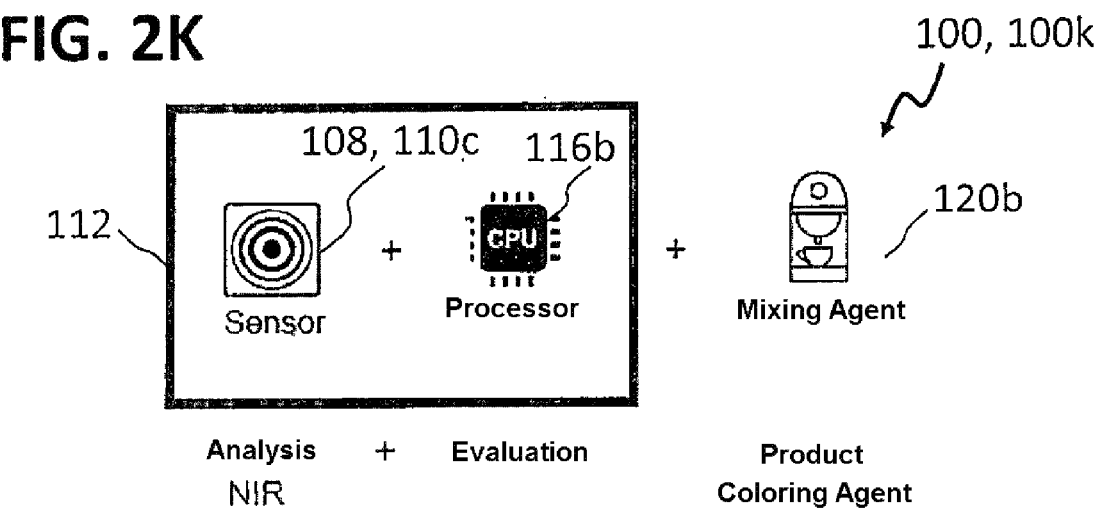

The device 100k of FIG. 2K has, as an integrated device 112, a near-infrared light sensor 110c for the determining of the hair damage, for example, cysteic acid content and/or for the determining of a hair status, and a data processing device 116*b* integrated therewith, and further a mixing device 120*b* for producing a coloring agent. The integrated device 112 can have a processor and an optical or acoustic input and/or output device. The mixing device 120*b* can be separate. Alternatively, not illustrated, a sensor for detecting fluorescent light can be used instead of the NIR sensor 110*c*.

FIG. 3A to 2M respectively illustrate a device 100*l* to 100*w* for providing a hair treatment agent according to various embodiments. In each case, the sensor device 108, the data processing device 116*c* and the mixing device 120 can be formed as separate devices. The data processing device 116*c* can be part of a smart mirror.

The device 100*l* of FIG. 3A has a generic sensor 110*a*, a data processing device 116*c* as part of a smart mirror 110*c*, and a generic mixing device 120. The generic sensor 110*a* can be, for example, a brush having at least one sensor 110*a*.

The device 100*m* of FIG. 3B has a smart terminal with microscope (attachment) 110*b*, a data processing device 116*c* as part of a smart mirror 110*c*, and a generic mixing device 120.

The device 100*n* of FIG. 3C has a generic sensor 110*a*, a data processing device 116*c* as part of a smart mirror 110*c*, and a generic mixing device 120. The generic sensor 110*a* can be, for example, a brush having at least one sensor 110*a*. Data can be transmitted from the sensor 110*a* to the smart mirror 116*c* as a signal 114, and the smart mirror 116*c* can transmit the composition of the hair treatment agent to the mixing device 120 as a signal 118.

The device 100*o* of FIG. 3C has a smart terminal with microscope (attachment) 110*b*, a data processing device 116*c* as part of a smart mirror 110*c*, and a generic mixing device 120. Data can be transmitted from the sensor 110*a* to the smart mirror 116*c* as a signal 114, and the smart mirror 116*c* can transmit the composition of the hair treatment agent to the mixing device 120 as a signal 118.

The device 100*p* of FIG. 3E has a generic sensor 110*a*, a data processing device 116*c* as part of a smart mirror 110*c* and a mixing device 120*a* for producing a care agent. The generic sensor 110*a* can be, for example, a brush having at least one sensor 110*a*. Data can be transmitted from the sensor 110*a* to the smart mirror 116*c* as a signal 114, and the smart mirror 116*c* can transmit the composition of the hair treatment agent to the mixing device 120*a* as a signal 118.

The device 100*q* of FIG. 3F has a smart terminal with microscope (attachment) 110*b*, a data processing device 116*c* as part of a smart mirror 110*c*, and a mixing device 120*a* for producing a care agent. Data can be transmitted from the sensor 110*a* to the smart mirror 116*c* as a signal 114, and the smart mirror 116*c* can transmit the composition of the hair treatment agent to the mixing device 120*a* as a signal 118.

The device 100*r* of FIG. 3G has a sensor 110*c* for near-infrared light for the determining of the hair damage, for example, based on cysteic acid content, and/or for the determining of a hair status, a data processing device 116*c* as part of a smart mirror 110*c*, and a mixing device 120*a* for producing a care agent. Data can be transmitted from the sensor 110*c* to the smart mirror 116*c* as a signal 114, and the smart mirror 116*c* can transmit the composition of the hair treatment agent to the mixing device 120*a* as a signal 118. Alternatively, not illustrated, a sensor for detecting fluorescent light can be used instead of the NIR sensor 110*c*.

The device 100*s* of FIG. 3H has a microphone 110*d* for determining of the surface roughness, a data processing device 116*c* as part of a smart mirror 110*c*, and a mixing device 120*a* for producing a care agent. Data can be transmitted from the sensor 110*c* to the smart mirror 116*c* as a signal 114, and the smart mirror 116*c* can transmit the composition of the hair treatment agent to the mixing device 120*a* as a signal 118.

Figure 3J:
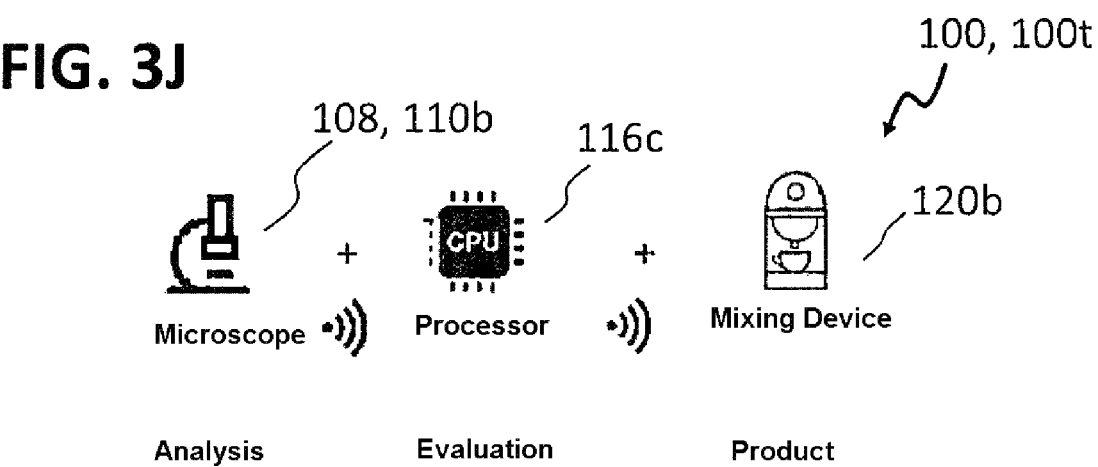

The device 100*t* of FIG. 3J has a smart terminal with microscope (attachment) 110*b* for the determining of the hair damage (for example, stretching damage), a data processing device 116*c* as part of a smart mirror 110*c*, and a mixing device 120*b* for producing a hair coloring agent. Data can be transmitted from the sensor 110*a* to the smart mirror 116*c* as a signal 114, and the smart mirror 116*c* can transmit the composition of the hair treatment agent to the mixing device 120*a* as a signal 118.

Figure 3K:
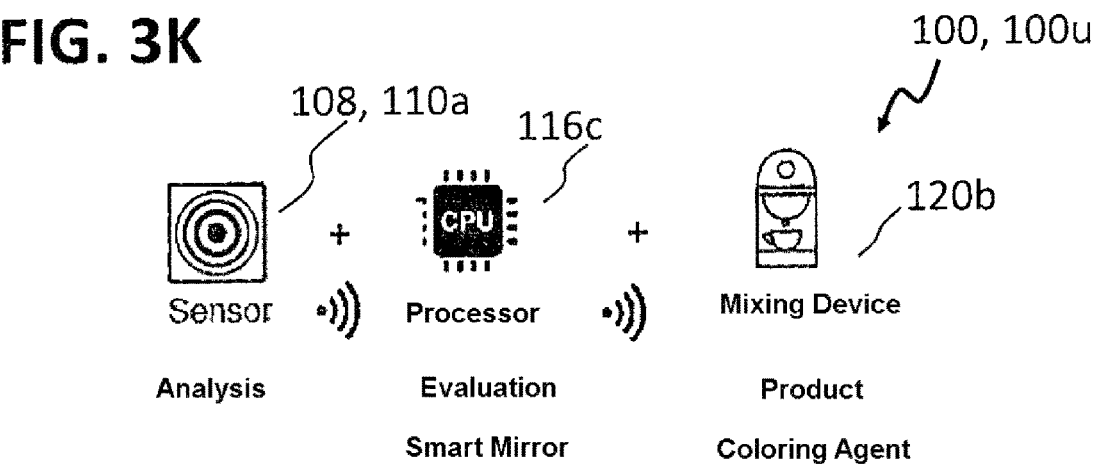

The device 100*u* of FIG. 3K has a generic sensor 110*a*, a data processing device 116*c* as part of a smart mirror 110*c* and a mixing device 120*b* for producing a hair coloring agent. The generic sensor 110*a* can be, for example, a brush having at least one sensor 110*a*. Data can be transmitted from the sensor 110*a* to the smart mirror 116*c* as a signal 114, and the smart mirror 116*c* can transmit the composition of the hair treatment agent to the mixing device 120*a* as a signal 118.

Figure 3L:
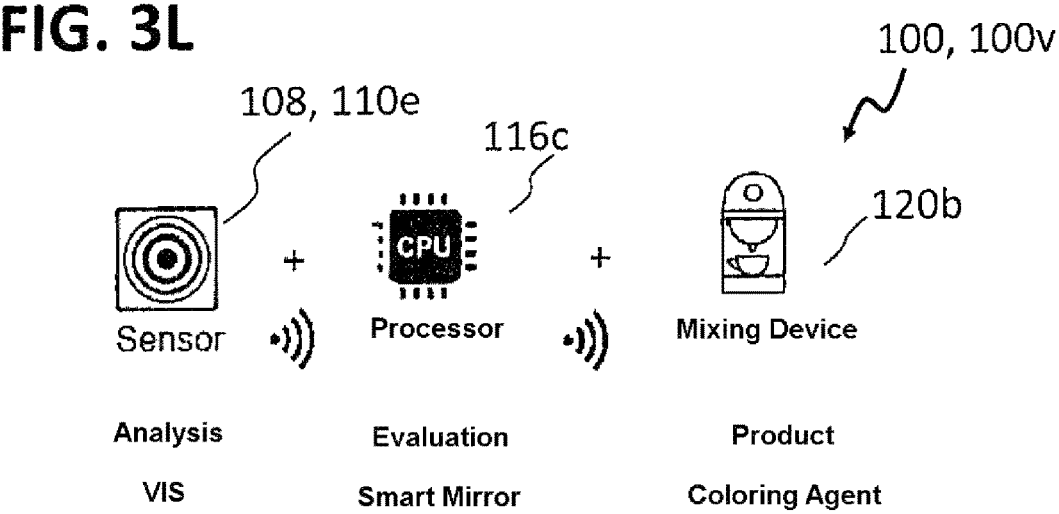

The device 100*v* of FIG. 3L has a sensor 110*e* for visible light for the determining of the hair color, for example, a digital color camera or a VIS sensor, a data processing device 116*c* as part of a smart mirror 110*c*, and a mixing device 120*b* for producing a hair coloring agent. Data can be transmitted from the sensor 110*e* to the smart mirror 116*c* as a signal 114, and the smart mirror 116*c* can transmit the composition of the hair treatment agent to the mixing device 120*a* as a signal 118.

Figure 3M:
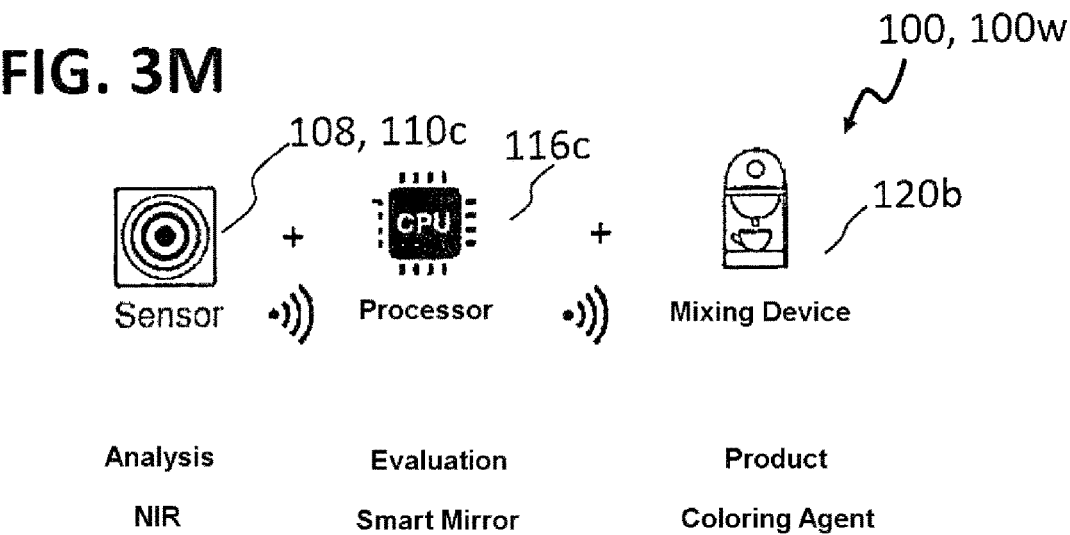

The device 100*w* of FIG. 3M has a sensor 110*c* for near-infrared light for the determining of the hair damage, for example, based on cysteic acid content, and/or for the determining of a hair status, a data processing device 116*c* as part of a smart mirror 110*c*, and a mixing device 120*a* for producing a hair coloring agent. Data can be transmitted from the sensor 110*c* to the smart mirror 116*c* as a signal 114, and the smart mirror 116*c* can transmit the composition of the hair treatment agent to the mixing device 120*a* as a signal 118. Alternatively, not illustrated, a sensor for detecting fluorescent light can be used instead of the NIR sensor 110*c*. In a further alternative, not illustrated, a sensor for detecting visible light and (N)IR light can be used instead of the NIR sensor 110*c*.

Figure 4A:
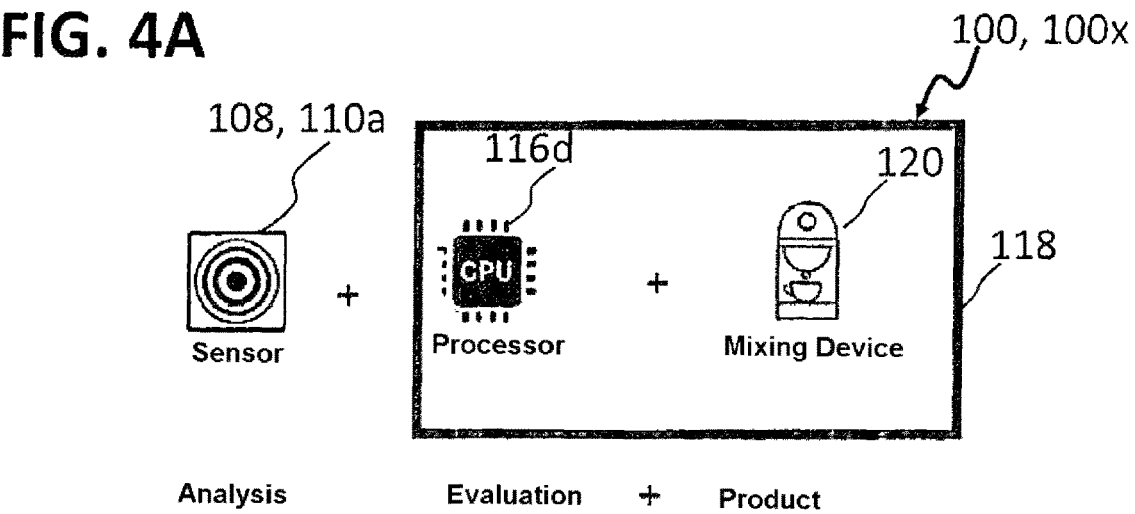

The device 100*x* of FIG. 4A has a generic sensor 110*a* and, as an integrated device 118, a data processing device 116*d* and a generic mixing device 120. The generic sensor 110*a* can be, for example, a brush having at least one sensor 110*a*. The integrated device 118 can be a mixing device 120 with a processor and an optical and/or acoustic input and/or output device.

Figure 4B:
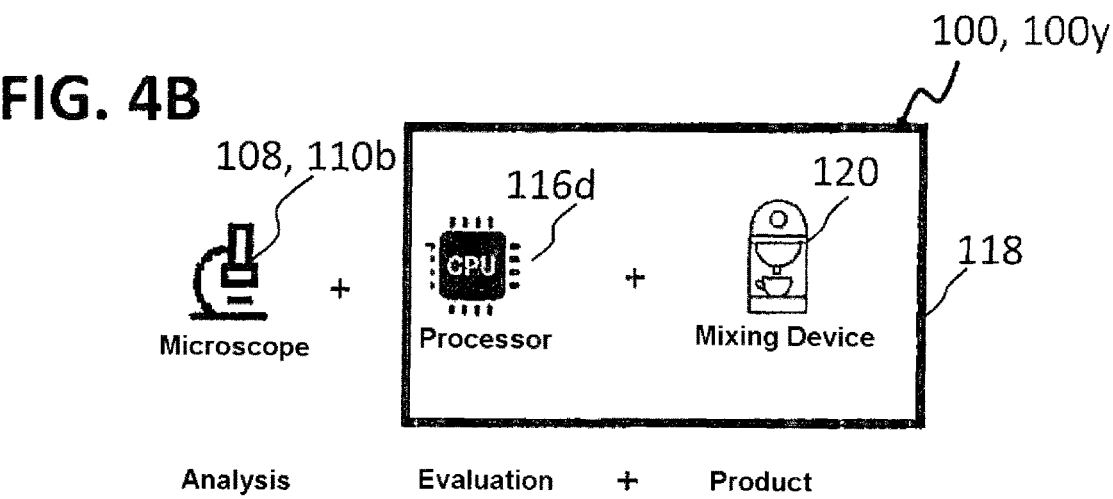

The device 100*y* of FIG. 4B has a smart terminal with a microscope (attachment) 110*b* and, as an integrated device 118, a data processing device 116*d* and a generic mixing device 120. The integrated device 118 can be a mixing device 120 with a processor and an optical and/or acoustic input and/or output device.

Figure 4C:
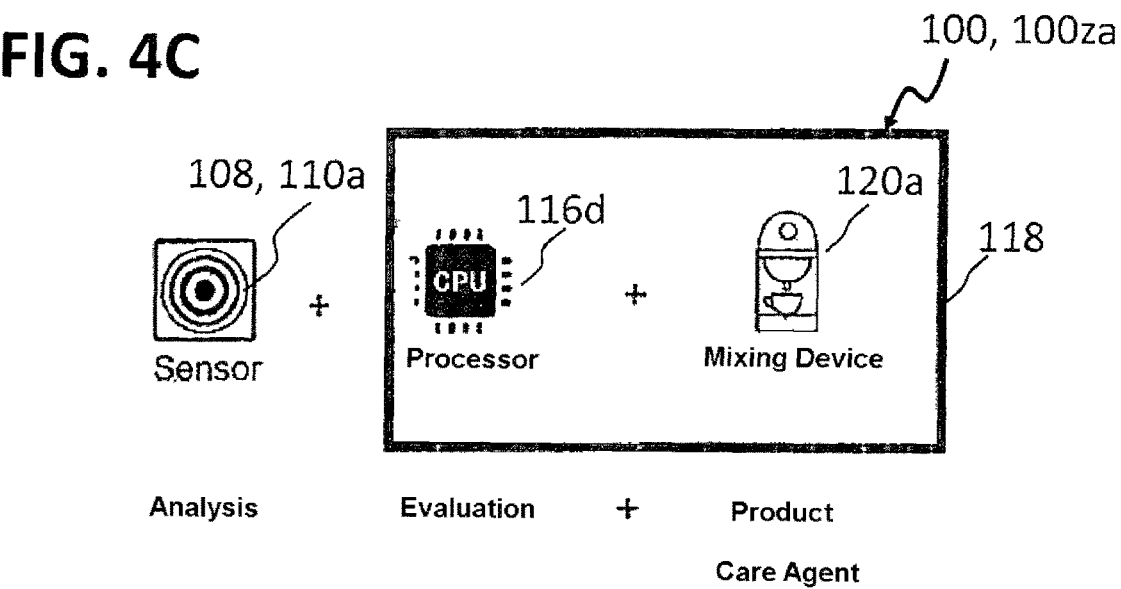

The device 100*za* of FIG. 4C has a generic sensor 110*a* and, as an integrated device 118, a data processing device 116*d* and a mixing device 120*a* for producing a care agent. The generic sensor 110*a* can be, for example, a brush having at least one sensor 110*a*. The integrated device 118 can be a mixing device 120 with a processor and an optical and/or acoustic input and/or output device.

The device 100*zb* of FIG. 4D has a smart terminal with microscope (attachment) 110*b* and, as an integrated device 118, a data processing device 116*d* and a mixing device 120*a* for producing a care agent. The integrated device 118 can be a mixing device 120 with a processor and an optical and/or acoustic input and/or output device.

The device 100zc of FIG. 4E has a sensor 110c for near-infrared light for the determining of the hair damage, for example, based on cysteic acid content, and/or for the determining of the hair status, and as an integrated device 118, a data processing device 116d and a mixing device 120a for producing a care agent. The integrated device 118 can be a mixing device 120 with a processor and an optical and/or acoustic input and/or output device. Alternatively, not illustrated, a sensor for detecting fluorescent light can be used instead of the NIR sensor 110c.

The device 100zd of FIG. 4F has a microphone 110d for the determining of the surface roughness, and as an integrated device 118, a data processing device 116d and a mixing device 120a for producing a care agent. The integrated device 118 can be a mixing device 120 with a processor and an optical and/or acoustic input and/or output device.

Figure 4G:
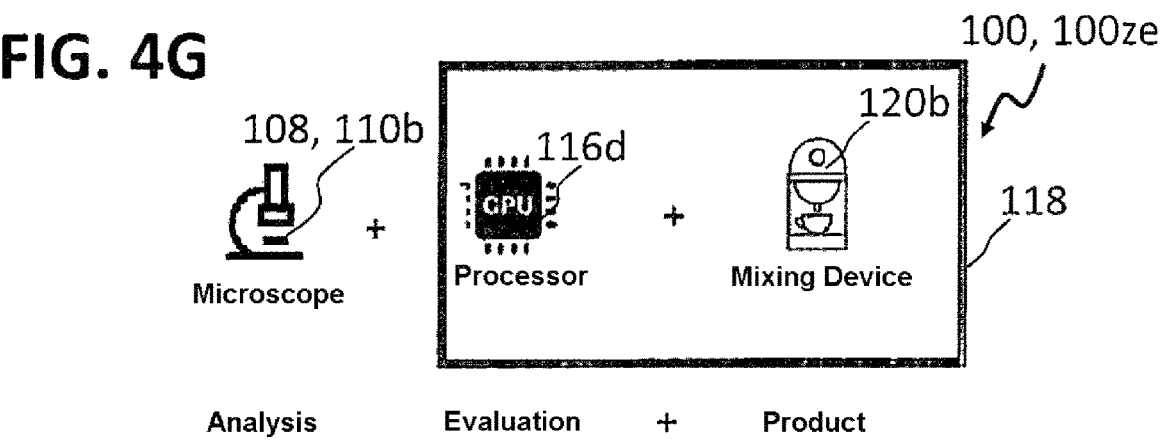

The device 100ze of FIG. 4G has a smart terminal with microscope (attachment) 110b and, as an integrated device 118, a data processing device 116d and a mixing device 120a for producing a hair coloring agent. The integrated device 118 can be a mixing device 120 with a processor and an optical and/or acoustic input and/or output device.

Figure 4H:
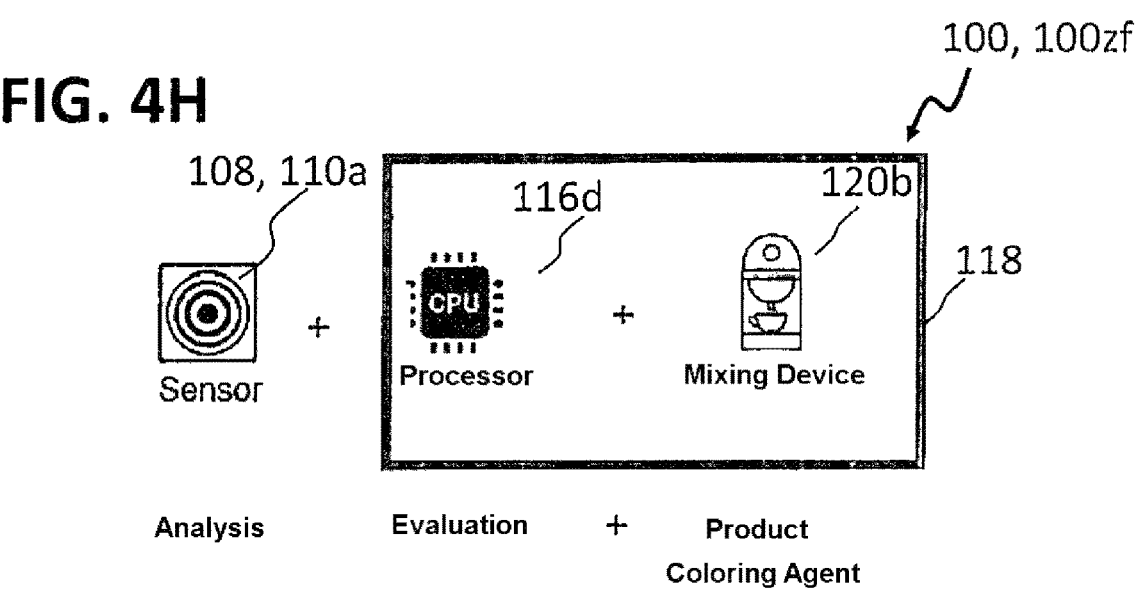

The device 100zg of FIG. 4H has a generic sensor 110a and, as an integrated device 118, a data processing device 116d and a mixing device 120a for producing a hair coloring agent. The generic sensor 110a can be, for example, a brush having at least one sensor 110a. The integrated device 118 can be a mixing device 120 with a processor and an optical and/or acoustic input and/or output device.

Figure 4J:
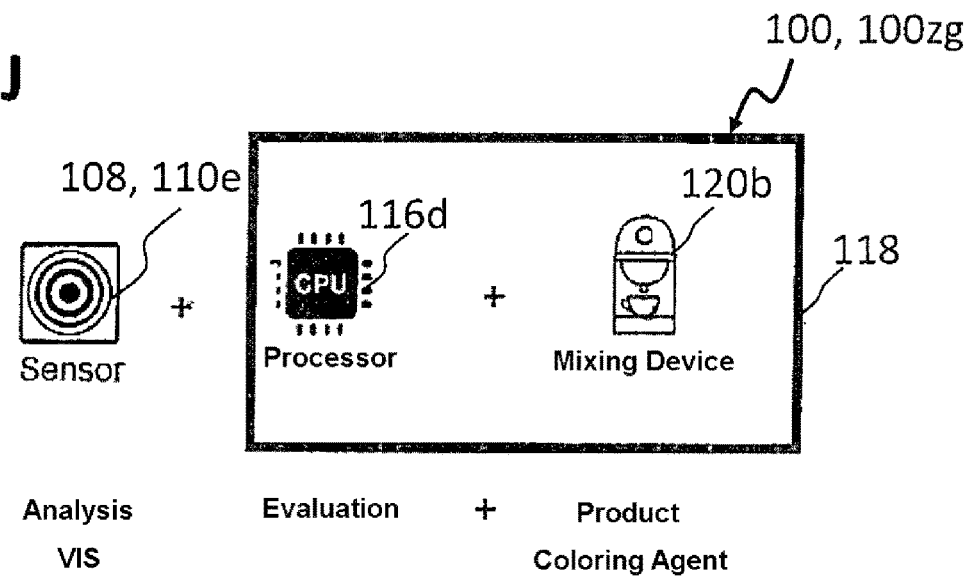
Figure 4K:
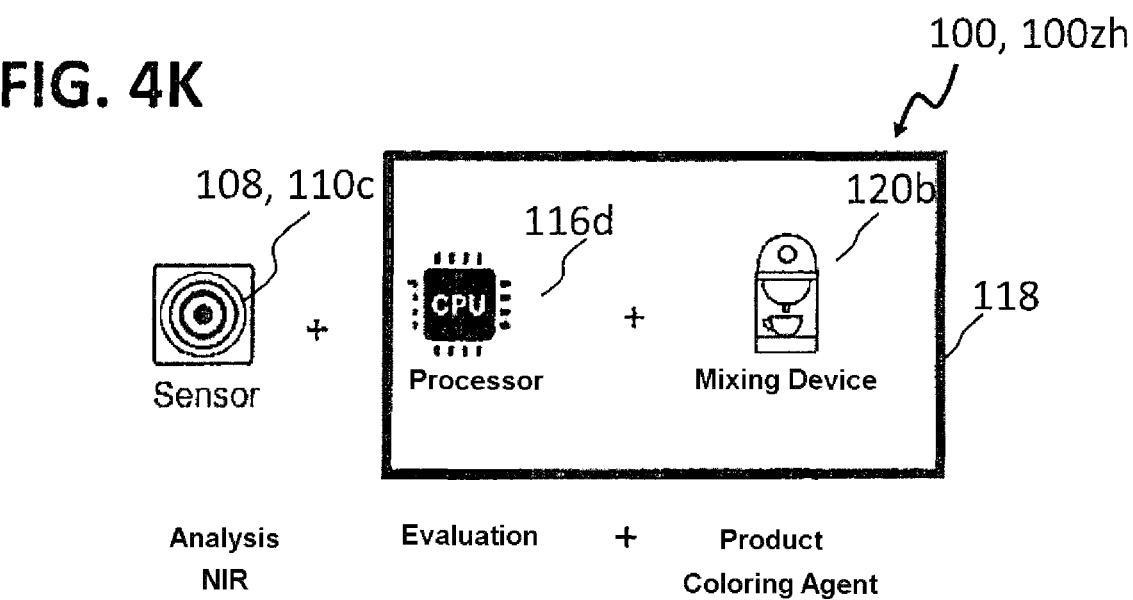

The device 100zg of FIG. 4J has a sensor 110e for visible light for the determining of the hair color, for example, a digital color camera or a VIS sensor, and, as an integrated device 118, a data processing device 116d and a mixing device 120b for producing a hair coloring agent. The integrated device 118 can be a mixing device 120 with a processor and an optical and/or acoustic input and/or output device.

The device 100zh of FIG. 4E has a sensor 110c for near-infrared light for the determining of the hair damage, for example, based on cysteic acid content, and/or for the determining of the hair status, and as an integrated device 118, a data processing device 116d and a mixing device 120a for producing a hair coloring agent. The integrated device 118 can be a mixing device 120 with a processor and an optical and/or acoustic input and/or output device. Alternatively, not illustrated, a sensor for detecting fluorescent light can be used instead of the NIR sensor 110c. In a further alternative, not illustrated, a sensor for detecting visible light and (N)IR light can be used instead of the NIR sensor 110c.

FIG. 5 illustrates a flowchart 500 of a method for providing a hair treatment agent according to various embodiments. A device according to various embodiments as described above can be used for executing the method.

The method can have a detecting of at least one sensor value on hair of a user by employing at least one portable sensor (at 510), a determining of a hair condition of a user be employing the detected at least one sensor value (at 520), a computer-assisted determining of an agent for hair treatment including the determined hair condition (at 530) and preparing the determined user-specific hair treatment agent by employing a hair treatment agent mixing device (at 540).

In various embodiments, the determining of the hair condition can have at least a determining of a degree of damage to the hair.

In various embodiments, the determining of the hair condition can have at least a determining of a hair status.

Further advantageous embodiments of the method are apparent from the description of the device and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A device for providing a hair treatment agent, comprising:
   a portable sensor device having at least one sensor for capturing a reflected light from a hair of a user;
   a memory for storing a relationship between a cysteic acid content value and a measure of light absorption intensity, wherein the relationship is determined in response to a plurality of light absorption measurements made on a plurality of hair samples having a known cysteic acid content;
   a data processing device for determining a light absorption intensity of the hair of the user in response to the reflected light, estimating a cysteic acid content of the hair of the user in response to the light absorption intensity and the relationship between the cysteic acid content value and the measure of light absorption intensity, and for determining of a user-specific hair treatment agent using the cysteic acid content; and
   a hair treatment agent mixer configured to prepare the user-specific hair treatment agent wherein the user-specific hair treatment agent is one of a hair care agent, a hair coloring agent and a hair styling agent.

2. The device according to claim 1,
   wherein the at least one sensor includes a microphone for determining a surface roughness of the hair.

3. The device according to claim 1,
   wherein the data processing device is part of a smartphone, tablet or a smart mirror.

4. The device according to claim 1,
   wherein the portable sensor device and the data processing device form an integrated portable device.

5. The device according to claim 1,
   wherein the at least one sensor includes at least one optical sensor for determining a hair color of the user.

6. A method of providing a hair treatment agent comprising:
   capturing a reflected light from a hair of a user by employing a sensor device having at least one portable sensor wherein the at least one portable sensor includes at least one optical sensor;
   determining a light absorption intensity of the hair of the user in response to the reflected light and estimating a cysteic acid content of the hair of the user in response to the light absorption intensity, wherein the cysteic acid content is estimated in response to a stored relationship between a cysteic acid content value and a measure of light absorption intensity, wherein the relationship is determined in response to a plurality of light absorption measurements made on a plurality of hair samples having a known cysteic acid content;

computer-assisted determining a user-specific hair treatment agent in response to the cysteic acid content, wherein the user-specific treatment agent includes at least one of a hair coloring agent, a hair care agent and a hair styling agent; and preparing the user-specific hair treatment agent.

7. The method according to claim 6, wherein determining the user-specific hair treatment agent includes determining a surface roughness of the hair.

8. The method according to claim 6, wherein determining the user-specific hair treatment agent includes determining a hair color of the user.

9. The method of claim 6, further comprising:
providing a treatment goal by the user.

10. The method of claim 6, further comprising:
transmitting a value representative of the reflected light from the sensor device to a data processing device and communicating the user-specific hair treatment agent from the data processing device to the hair treatment agent mixing device.

11. The method according to claim 10, wherein
the data processing device is further configured to transmit the light absorption intensity or a determined hair condition to an external data processing device, and is further configured to receive a result from the external data processing device.

12. A device for providing a hair treatment agent, comprising:
a portable sensor device having at least one optical sensor for capturing a reflected light from a hair of a user and a microphone for determining a surface roughness of the hair;

a memory for storing a relationship between a cysteic acid content value and a measure of light absorption intensity, wherein the relationship is determined in response to a plurality of light absorption measurements made on a plurality of hair samples having a known cysteic acid content;

a data processing device for determining a light absorption intensity of the hair of the user in response to the reflected light, estimating a cysteic acid content of the hair of the user in response to the light absorption intensity and the relationship between the cysteic acid content value and the measure of light absorption intensity, and for determining of a user-specific hair treatment agent in response to the cysteic acid content; and a hair treatment agent mixer configured to prepare the user-specific hair treatment agent, wherein the user-specific hair treatment agent is one of a hair care agent, a hair coloring agent and/or a hair styling agent.

13. The device according to claim 12,
wherein the at least one optical sensor is configured to determine a cysteine acid content of the hair.

* * * * *